United States Patent [19]

Adachi et al.

[11] Patent Number: 5,142,029
[45] Date of Patent: * Aug. 25, 1992

[54] SILVER HALIDE PHOTOGRAPHIC MATERIAL CONTAINING A COMPOUND WITH VARIABLE DEVELOPMENT RESTRAINING ABILITY

[75] Inventors: Keiichi Adachi, Shingo Sato, Shigeo Hirano, Koki Nakamura, Morio Yagihara, Isamu Ito, Tadashi Ikeda, Keniahi Kuwabara, all of Kanagawa, Japan

[73] Assignee: Fuji Photo Film Co., Ltd., Kanagawa, Japan

[*] Notice: The portion of the term of this patent subsequent to Apr. 26, 2005 has been disclaimed.

[21] Appl. No.: 741,229

[22] Filed: Aug. 5, 1991

Related U.S. Application Data

[63] Continuation of Ser. No. 370,138, Jun. 23, 1989, abandoned, which is a continuation of Ser. No. 42,611, Apr. 21, 1987, abandoned, which is a continuation of Ser. No. 751,905, Jul. 5, 1985, abandoned.

[30] Foreign Application Priority Data

Jul. 4, 1984 [JP] Japan ............... 59-13808
Apr. 4, 1985 [JP] Japan ............... 60-71768

[51] Int. Cl.$^5$ ......................... G03C 7/388
[52] U.S. Cl. ......................... 430/544; 430/566; 430/157; 430/955
[58] Field of Search ............ 430/505, 544, 566, 955, 430/957

[56] References Cited

U.S. PATENT DOCUMENTS

| | | | |
|---|---|---|---|
| 3,379,529 | 4/1968 | Porter et al. ............ | 430/566 |
| 3,930,863 | 1/1976 | Shiba et al. ............ | 430/505 |
| 4,144,071 | 3/1979 | Shiba et al. . | |
| 4,199,355 | 4/1980 | Hinshaw et al. ............ | 430/955 |
| 4,248,962 | 2/1981 | Lau ............ | 430/544 |
| 4,310,621 | 1/1982 | Odenwalder et al. ............ | 430/959 |
| 4,332,878 | 6/1982 | Akimura et al. ............ | 430/264 |
| 4,345,024 | 8/1982 | Hirano et al. ............ | 430/382 |
| 4,358,532 | 11/1982 | Koyama et al. ............ | 430/955 |
| 4,459,351 | 7/1984 | Adin et al. ............ | 430/566 |
| 4,477,563 | 10/1984 | Ichijima et al. ............ | 430/544 |
| 4,501,898 | 2/1985 | Hirano et al. ............ | 548/336 |
| 4,546,073 | 10/1985 | Bergthaller et al. ............ | 430/955 |
| 4,636,456 | 1/1987 | Takahashi et al. ............ | 430/456 |
| 4,724,199 | 2/1988 | Kobayashi et al. . | |
| 4,740,453 | 4/1988 | Nakamura et al. ............ | 430/505 |

*Primary Examiner*—Charles L. Bowers, Jr.
*Assistant Examiner*—Janet C. Baxter
*Attorney, Agent, or Firm*—Sughrue, Mion, Zinn Macpeak & Seas

[57] ABSTRACT

The compounds in a preferred form are represented by general formula (I):

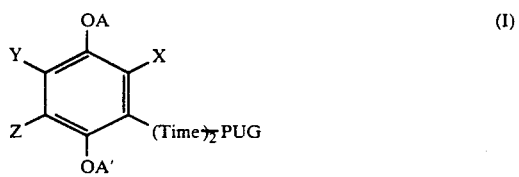

wherein A and A' are each a group which can be hydrolyzed by hydrogen or alkali; X, Y and Z are each hydrogen, a halogen atom, a substituted or unsubstituted alkyl group, a substituted or unsubstituted alkoxy group, a substituted or unsubstituted aryl group, a thioalkyl group or an electron-withdrawing group; PUG is a group released by a reaction with a light-exposed silver halide and/or the oxidized product of the developing agent, Time is a timing group; $-(Time)_t$-PUG is a group released as $\ominus-(Time)_t$-PUG first when the oxidation-reduction moiety causes a cross reaction during the development and becomes an oxidized product, and is bonded to the benzene nucleus via a sulfur atom, a nitrogen atom or a selenium atom; and t is 0 or 1.

10 Claims, No Drawings

SILVER HALIDE PHOTOGRAPHIC MATERIAL CONTAINING A COMPOUND WITH VARIABLE DEVELOPMENT RESTRAINING ABILITY

This is a continuation of application Ser. No. 07/370,138 filed Jun. 23, 1989, now abandoned, which is a continuation of application Ser. No. 07/042,611 filed Apr. 21, 1987, now abandoned, which is a continuation of application Ser. No. 06/751,905 filed Jul. 5, 1985, now abandoned.

FIELD OF THE INVENTION

The present invention relates to a silver halide photographic material containing a group which may release a photographically useful group through an oxidation step during photographic processing.

BACKGROUND OF THE INVENTION

Numerous compounds are known which release photographically useful groups in accordance with the image density during development. Hydroquinone derivatives (e.g., DIR hydroquinone) are known as compounds which release development restrainers in correspondence to image density during development. Exemplary compounds known as DIR hydroquinones include those described in U.S. Pat. Nos. 3,379,529 and 3,620,746 and Japanese Patent Application (OPI) No. 129,536/74. (The term "OPI" as used herein refers to a "published unexamined Japanese patent application.")

As in known from the above-cited references, DIR hydroquinone is used to obtain the so-called DIR effects, such as tone control, finer-grain images, improved sharpness and better color reproduction and the like. Conventional DIR hydroquinones show a certain degree of these effects, but further improvement has been required.

In particular, known DIR hydroquinones have the following disadvantage:

As the restrainer released during development becomes diffused from the sensitive material into the developing solution, it is accumulated in the solution. As a result, the solution shows restraining effects. If a large quantity of the sensitive material is treated on a continuous basis, as in the method commonly employed on a commercial scale, it is difficult to always obtain a constant color tone. Thus, the contamination of the development solution with the restrainer released by DIR hydroquinone is a serious problem.

In order to solve this problem, various measures have been taken as a matter of convenience, but they all have some disadvantages and no fundamental solution has not yet been known. For example, the following methods are known:

(1) Restriction of the amount of DIR hydroquinone used for the development;

(2) Frequent change of the developer solution for a new supply; and (3) Incorporation in the sensitive material of a microcrystal emulsion layer free from any substantial photographic sensitivity as a scavenger for the restrainer released from the sensitive layer.

However, these methods all ave disadvantages such as the limitation of photographic improvement and a large increase in cost.

SUMMARY OF THE INVENTION

The DIR compounds such as DIR hydroquinone of the present invention provide a fundamental solution to the aforementioned problems. In other words, it is an object of the present invention to provide by the use of a novel DIR compound a photographic material which gives excellent sharpness to the image.

It is another object of the present invention to provide, by the use of a novel DIR compound, a photographic material which shows excellent performance in color reproduction.

It is still another object of the present invention to provide a photographic material which is suitable for a process which involves no contamination of the developing solution and wherein the solution is continuously reused.

The above-identified objects of the present invention have been met y incorporating into the silver halide photographic material at least one compound having a group which, after being released from the compound by redox reaction, becomes converted into a compound having development restraining properties and which becomes further converted in the developing solution to a compound which has no substantial development restraining ability or which shows a marked decrease in such ability.

In order to accomplish the objects of the present invention, it is preferable to use the compound of formula (I):

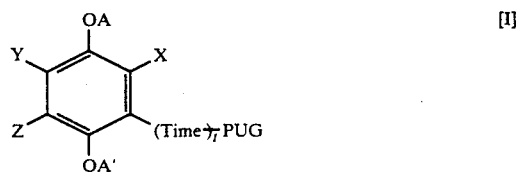

wherein A and A' are each a group which can be hydrolyzed by hydrogen or alkali, such as acyl or alkoxycarbonyl group; X, Y and Z are each hydrogen, a halogen atom (e.g., chlorine, bromine and iodine), a substituted or unsubstituted alkyl group (preferably having 1 to 20 carbon atoms, such as methyl, ethyl, propyl, aryl, octyl, dodecyl, cyclohexyl, hydroxyethyl, sulfonylethyl and carboxypropyl groups, provided that Y and Z may form a 5- or 6-membered ring through a methylene chain), a substituted or unsubstituted alkoxy group (preferably having 1 to 20 carbon atoms, such as methoxy, ethoxy, butyloxy, octyloxy, hexadecyloxy and methoxyethoxy groups), a substituted or unsubstituted aryl group (preferably having 6 to 20 carbon atoms, such as dodecylphenyl, tolyl, p-methoxyphenyl and p-chlorophenyl groups), a alkylthio group (preferably having 1 to 20 carbon atoms, such as methylthio, butylthio, octylthio and hexadecylthio groups), and an electron withdrawing group.

Exemplary electron-withdrawing groups include:

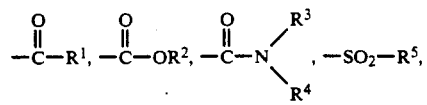

-continued

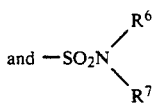

wherein $R^1$ to $R^7$ are each a substituted or unsubstituted alkyl group (preferably having 1 to 30 carbon atoms, such as methyl, ethyl, propyl, aryl, butyl, octyl, dodecyl, adamantyl, cyclohexyl, methoxyethyl, hydroxyethyl, sulfoethyl and carboxypropyl groups), a substituted or unsubstituted aryl group (preferably having 6 to 30 carbon atoms, such as dodecylphenyl, tolyl, p-methoxyphenyl, phenyl, p-chlorophenyl and m-nitrophenyl groups) and a substituted or unsubstituted aralkyl group (preferably having 7 to 30 carbon atoms, such as benzyl and phenethyl groups).

In formula (I), PUG is a group released by a reaction with a light-exposed silver halide and/or the oxidized product of the developing agent, and is preferably represented by formula (II):

   (II)

wherein the group represented by AF is preferably one of the following formulas, the substitution sites of CCD also being shown:

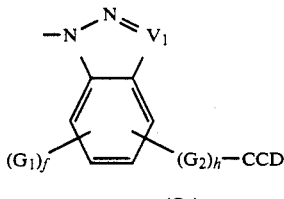   Formula (P - 1)

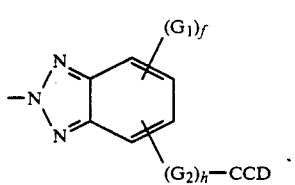   Formula (P - 2)

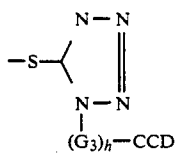   Formula (P - 3)

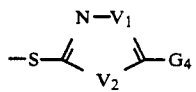   Formula (P - 4)

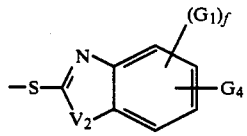   Formula (P - 5)

wherein $G_1$ is hydrogen, a halogen atom, an alkyl group (e.g., methyl and ethyl groups), an acylamino group (e.g., benzamido and hexanamido groups), an alkoxy group (e.g., methoxy and benzyloxy groups), a sulfonamido group (e.g., methanesulfonamido and benzenesulfonamido groups), an aryl groups (e.g., phenyl and 4 chlorophenyl groups). an alkylthio group (e.g., methylthio and butylthio groups), an alkylamino group (e.g., a cyclohexylamino group), an anilino group (e.g., anilino and 4-methoxycarbonylanilino groups), an amino group, an alkoxycarbonyl group (e.g., methoxycarbonyl and butoxycarbonyl groups), an acyloxy group (e.g., acetyl, butanoyl and benzoyl groups), a nitro group, a cyano group, a sulfonyl group (e.g., butanesulfonyl and benzenesulfonyl groups), an aryloxy group (e.g., phenoxy and naphthyloxy groups), a hydroxy group, a thioamido group (e.g., butanethioamido and benzenethiocarbonamido groups), a carbamoyl group (e.g., carbamoyl and N-arylcarbamoyl groups), a sulfamoyl group (sulfamoyl and N-arylsulfamoyl groups), a carboxyl group, a ureido group (e.g., ureido and N-ethylureido groups) or an aryloxycarbonyl group (e.g., phenoxycarbonyl and 4-methoxycarbonyl groups);

wherein $G_2$ is any one of the substituents listed for $G_1$ which may form a divalent group:

wherein $G_3$ is a substituted or unsubstituted alkylene group or substituted or unsubstituted arylene group and may be interrupted by an ethyl, ester, thioether, amido, ureido, imido, sulfon or sulfonamido bond or a carbonyl group. These bonding groups and alkylene and arylene groups may be linked together to form a divalent group;

wherein $V_1$ is a nitrogen atom or a methine group, and $V_2$ is an oxygen atom, sulfur atom,

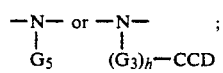

wherein $G_4$ is any one of the substituents listed for $G_1$ or $(G_3)_h$-CCD, and $G_5$ is a hydrogen atom, an alkyl group (e.g., methyl and ethyl groups) or an aryl group (e.g., phenyl and naphthyl groups); and wherein f is an integer of 1 or 2, and h is 0 or 1.

When f is 2 the two $G_1$'s may or may not be identical.

In formulas (P-4) and (P-5), at least one of the groups represented by $V_2$ and $G_4$ contains CCD.

In formulas (P-1), (P-2), (P-3), (P-4) and (P-5), when $G_1$, $G_2$, $G_3$, $G_4$ or $G_5$ contains an alkyl group portion, the alkyl group has 1 to 22, and preferably 1 to 10 carbon atoms and may be substituted or unsubstituted, straight-chain or branched, a chain or a ring, or saturated or unsaturated. When $G_1$, $G_2$, $G_3$, $G_4$ or $G_5$ contains an aryl group portion, the aryl group has 6 to 10 carbon atoms and is preferably a substituted or unsubstituted phenyl group.

In formula (II), the group represented by CCD is shown preferably by the following formulas (D-1) and (D-2) and formulas (D-3) to (D-16) which will follow later in this specification:

   Formula (D - 1)

   Formula (D - 2)

wherein $R^8$ and $R^9$ are each a substituted or unsubstituted alkyl (preferably having 1 to 10 carbon atoms, such as methyl, ethyl, 2,3-dichloropropyl, 2,2,3,3-tetrafluoropropyl, butoxycarbonyl, methylcyclohexylaminocarbonylmethyl, methoxyethyl and propargyl groups), a substituted or unsubstituted aryl group (preferably having 6 to 10 carbon atoms, such as phenyl, 3,4-methyleneoxyphenyl, p-methoxyphenyl, p-cyanophenyl and m-nitrophenyl groups), and a substituted or unsubstituted aralkyl group (preferably having 7 to 12 carbon atoms, such as benzyl and p-nitribenzyl groups).

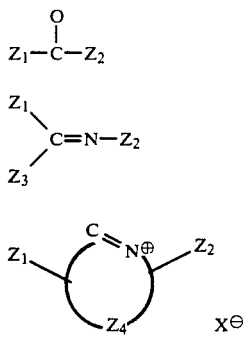

Formula (D - 3)

Formula (D - 4)

Formula (D - 5)

wherein $Z_1$ or $Z_2$ are each a bond to AF or one of the following:

a hydrogen atom, an alkylamino group (e.g., $CH_3$—NH— and

groups), alkyl group (e.g., methyl, propyl, methoxymethyl and benzyl groups), aryl group (e.g., phenyl, 4-chlorophenyl, naphthyl, 4-methoxyphenyl and 4-butaneamidophenyl groups), acylamido group (the nitrogen atom may be substituted; e.g., acetamido and benzamido groups) or a 4- or 7-membered substituted or unsubstituted heterocyclic group containing as the hetero-atom a nitrogen, sulfur or oxygen atom (e.g., 2-pyridyl, 2-pyrrolidyl, 4-imidazolyl and 3-chloro-5-pyrazolyl groups); and wherein $Z^3$ is a hydrogen atom, a halogen atom, an alkyl group (e.g., methyl and propyl groups), aryl group (e.g., phenyl, 4-chlorophenyl and naphthyl group), heterocyclic group (4- or 7-membered heterocyclic group containing as the hetero-atom one chosen from the group consisting of nitrogen, sulfur and oxygen atoms; e.g., 2-pyridyl and 2-pyrrolidyl groups), alkoxy group (e.g., methoxy and butoxy groups), acyl group (e.g., acetyl and benzoyl groups), carbamoyl group (the nitrogen atom may be substituted; e.g., N-butylcarbamoyl and N-phenylcarbamoyl groups), sulfamoyl group (the nitrogen atom may be substituted; e.g., N-phenylsulfamoyl group), sulfonyl group (e.g., propanesulfonyl and benzenesulfonyl groups), alkoxycarbonyl group (e.g., ethoxycarbonyl group), acylamino group (e.g., acetamido and benzamido groups), sulfonamido group (e.g., benzenesulfonamido group), alkylthio group (e.g., butylthio group) or ureido group (the nitrogen atom may be substituted; e.g., 3-phenylureido and 3-butylureido groups). $Z_1$ and $Z_3$, when taken together, may form a ring.

In formula (D-5), $Z_4$ is a group of atoms selected from the group consisting of carbon, nitrogen, oxygen and sulfur atoms which may form a 5- or 6-membered unsaturated heterocycle, and $X^\ominus$ is an organic sulfonic acid anion, an organic carboxylic acid anion, a halogen ion or an inorganic anion (e.g., tetrafluoroborate). Exemplary heterocycles formed by $Z_4$ include the rings of the following formulas wherein $Z_1$ may be bonded at a substitution site:

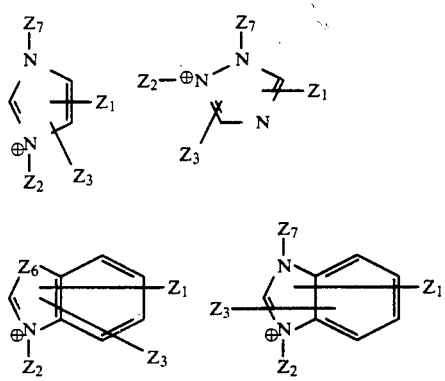

In the above formulas, $Z_7$ has the same meaning as the substituents listed for $Z_1$ or $Z_2$, and $Z_6$ is an oxygen atom or a sulfur atom.

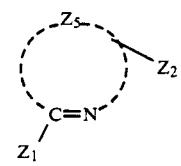

wherein $Z_1$ and $Z_2$ are as defined above, and $Z_5$ is a group of atoms selected from the group consisting of carbon, oxygen and nitrogen atoms which, together with

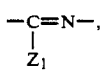

may form a 5- to 7-membered ring and which does not give aromatic group properties to

and which is preferably an alkylene group (which may be substituted, such as —$(CH_2)_4$—), an alkenylene group (which may be substituted, such as

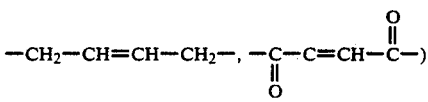

and a group of

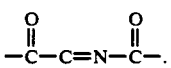

In formulas (D-3), (D-4), (D-5) and (D-6), when $Z_1$, $Z_2$, $Z_3$ or $Z_7$ contains an alkyl group portion, the alkyl group has 1 to 16 and preferably 1 to 10 carbon atoms, and may be substituted or unsubstituted, straight-chain or branched, a chain or ring, saturated or unsaturated. When $Z_1$, $Z_2$, $Z_3$ or $Z_7$ contains an aryl group portion, the aryl group has 6 to 10 carbon atoms and is preferably a substituted or unsubstituted phenyl group.

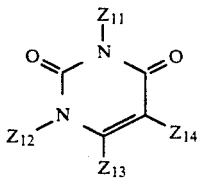

Formula (D - 7)

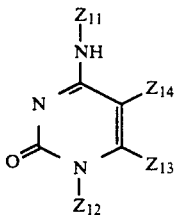

Formula (D - 8)

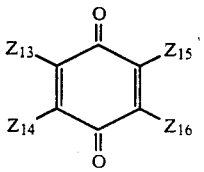

Formula (D - 9)

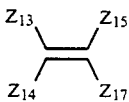

Formula (D - 10)

In formulas (D-7) to (D-10), at least one of $Z_{11}$ to $Z_{17}$ is one of the above-illustrated AF groups or a group containing an AF group.

In the above formulas, $Z_{11}$ and $Z_{12}$ are each a hydrogen atom, an alkyl group or aryl group or an AF group.

In the above formulas, $Z_{13}$, $Z_{14}$, $Z_{15}$ and $Z_{16}$ are each a hydrogen atom, an alkyl group, aryl group, halogen atom (e.g., Chlor atom), alkoxy group (e.g., methoxy and butoxy groups), aryloxy group (e.g., phenoxy, and p-carboxyphenoxy groups), arylthio group (e.g., phenylthio group), alkylthio group (e.g., methylthio and butylthio groups), alkoxycarbonyl group (e.g., ethoxycarbonyl and octylcarbonyl groups), aryloxycarbonyl group (e.g., phenoxycarbonyl group), alkanesulfonyl group (e.g., methanesulfonyl group), sulfamoyl group (e.g., sulfamoyl and methylsulfamoyl groups), carbamoyl group (e.g., carbamoyl and N-phenylcarbamoyl groups), ureido group (e.g., N-methylureido group), acyl group (e.g., acetyl and benzoyl groups), acylamino group (e.g., acetamido and benzamido groups), arylsulfonyl group (e.g., benzenesulfonyl group), heterocyclic group (5- or 6-membered ring wherein the hetero atom is chosen from the group consisting of nitrogen, oxygen and sulfur atoms, e.g., imidazolyl; 1,2,4-triazolyl, thiadiazolyl or oxadiazolyl groups), acyloxy group (e.g., acetyloxy group), nitro group, cyano group, carboxyl group, thiocarbamoyl group (e.g., phenylthiocarbamoyl group), sulfamoylamino group (e.g., N-phenylsulfamoylamino group), diacylamino group (e.g., diacetylamino group or allylideneamino group (e.g., benzilideneamino group) or an AF group.

$Z_{17}$ is one of the following groups, provided that AF may be bonded through one of the following groups which may form divalent groups: a halogen atom, an alkoxycarbonyl group, aryloxycarbonyl group, alkanesulfonyl group, sulfamoyl group, carbamoyl group, acyl group, diacylamino group, arylsulfonyl group, heterocyclic group, nitro group, cyano group, carboxyl group or sulfonamido group. Specific examples are those illustrated above for $Z_{13}$ to $Z_{16}$.

In formulas (D-7), (D-8), (D-9) and (D-10), when $Z_{11}$, $Z_{12}$, $Z_{13}$, $Z_{14}$, $Z_{15}$, $Z_{16}$ or $Z_{17}$ contains an alkyl group portion, the alkyl group has 1 to 16, and preferably 1 to 8 carbon atoms and may be substituted or unsubstituted, straight-chain or branched, a chain or ring, saturated or unsaturated. When $Z_{11}$, $Z_{12}$, $Z_{13}$, $Z_{14}$, $Z_{15}$, $Z_{16}$ or $R_{17}$ contains an aryl group portion, the aryl group has 6 to 10 carbon atoms and is preferably a substituted or unsubstituted phenyl group.

In formula (D-9), $Z_{15}$ and $Z_{16}$ may each form a divalent group and, when taken together, may form a ring (e.g., a benzene ring).

In formula (D-10), $Z_{15}$ and $Z_{16}$ may each form a divalent group and, when taken together, may form a ring (e.g., a benzothiazolylidene group).

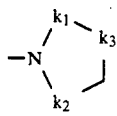

Formula (D-11)

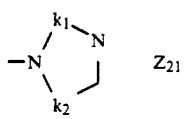

Formula (D-12)

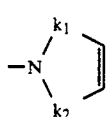

Formula (D-13)

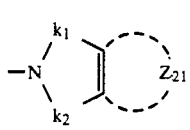

Formula (D-14)

wherein $Z_{21}$ is a saturated or unsaturated 6-membered ring; $k_1$ and $k_2$ are electron attractive groups (e.g.,

and $-SO_2-$); and $k_3$ is

(wherein R is an alkyl group having preferably not more than 6 carbon atoms).

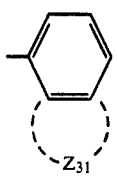

Formula (D-15)

(provided that h=0 in the above-illustrated formulas (P-1) to (P-5)).

Formula (D-16)

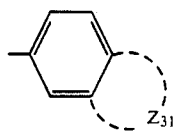

(provided that h=0 in the above-stated formulas (P-1) to (P-5)).

In these formulas, $Z_{31}$ is a group which may form a 5- or 6-membered lactone ring or a 5-membered cyclic imide.

In formula (I), $-(\text{Time})_t$PUG is a group released as $\ominus-(\text{Time})_t$PUG first when the oxidation-reduction moiety causes a cross reaction during the development and becomes an oxidized product, and is bonded to the benzene nucleus of formula (I) via a sulfur atom, a nitrogen atom or a selenium atom.

As the timing group of Time, there can be exemplified a group which releases PUG from $\ominus$Time-PUG released during the development, by way of one or more stage reactions Examples of Time include those described in U.S. Pat. Nos. 4,428,962 and 4,409,323, British Patent 2,096,783, U.S. Pat. No. 4,146,396, and Japanese Patent application (OPI) Nos. 146,828/76 and 56,837/82. Time can be used in combination of one or more of those described in the above-cited patents.

t is 0 or 1.

It is more preferable to use the compound of formula (III):

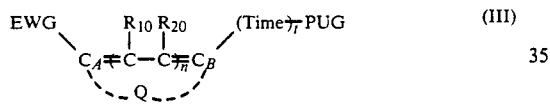

wherein Q is an atomic group which bonds to $C_A$ and $C_B$ and forms a substituted benzene ring-type oxidation-reduction moiety from which Time-PUG can be released first by oxidation during the photographic development processing; EWG is an electron-withdrawing group having a Hammett's $\sigma_{para}$ value exceeding 0.3; $C_A$ and $C_B$ are each a carbon atom which conjugates EWG with Time-PUG via a substituted ethylene bond or its vinylog, when the compound of formula (III) is oxidized; $R_{10}$ and $R_{20}$ are each a hydrogen atom or an appropriate substituent; Time and t are the same as defined above in formula (I); PUG is the same as defined above in formula (I), and when t is 0 (i.e., Time is a simple bond), it is a sulfur atom, a nitrogen atom or a selenium atom and is connected with $C_B$; and n is an integer of 0 or 1.

Examples of Q including

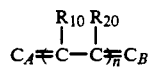

are shown below.

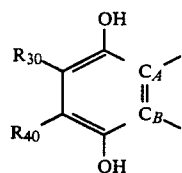
(a)

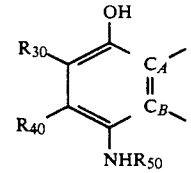
(b)

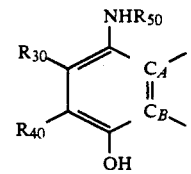
(c)

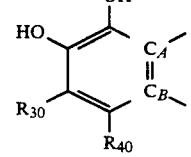
(d)

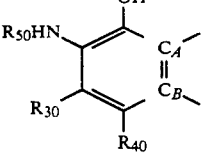
(e)

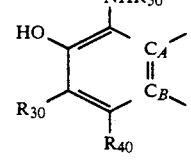
(f)

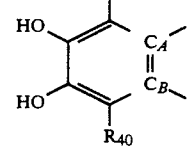
(g)

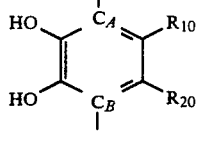
(h)

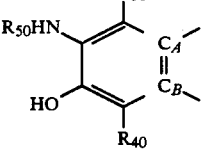
(i)

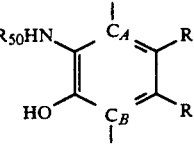
(j)

-continued

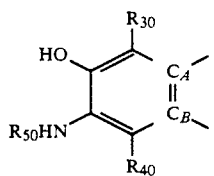
(k)

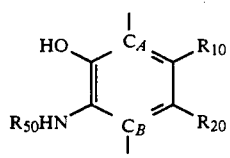
(l)

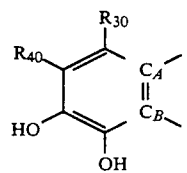
(m)

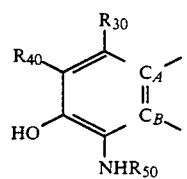
(n)

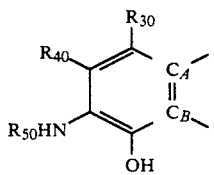
(o)

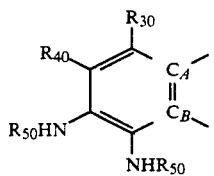
(p)

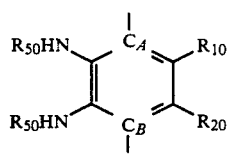
(q)

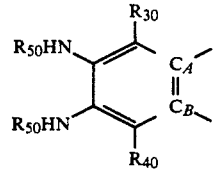
(r)

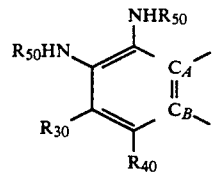
(s)

-continued

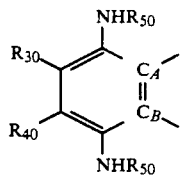
(t)

Among (a) to (t), (a), (b), (c), (d), (e), (f), (h), (j), (l), (m), (n), (o), and (t) are preferred; (a), (b), (c), (d), (e), and (f) are more preferred; and (a) is most preferred.

In formulas (a) to (t), $R_{10}$, $R_{20}$, $R_{30}$, and $R_{40}$ are each a hydrogen atom, a substituted or unsubstituted alkyl group having 1 to 30 carbon atoms (such as methyl, ethyl, isopropyl, 2-decyl, t-octyl, octadecyl, benzyl, phenethyl and 3-ethoxycarbonylpropyl groups), a substituted or unsubstituted aryl group having 6 to 30 carbon atoms (such as phenyl, 3-chlorophenyl, 4-cyanophenyl and naphthyl groups), a substituted or unsubstituted alkylthio group having 1 to 30 carbon atoms (such as methylthio, ethylthio, n-octylthio, 2-octhylthio, dodecylthio, 1-ethoxycarbonyl-1-decylthio and 2-cyanoethylthio groups), a substituted or unsubstituted arylthio group having 6 to 30 carbon atoms (such as phenylthio, 4-chlorophenylthio, 2-n-octyloxy-5-t-octylphenylthio, 4-t-butylphenylthio and 1-naphthylthio groups), a substituted or unsubstituted alkoxy group having 1 to 30 carbon atoms (such as methoxy, ethoxy, allyloxy, 2-propyloxy, octadecyloxy and benzyloxy groups), a substituted or unsubstituted aryloxy groups having 6 to 30 carbon atoms (such as phenoxy, 4-chlorophenoxy, 4-acetylaminophenoxy, 2-acetylamino-4-butanesulfonylphenoxy, 3-cyanophenoxy, 3-docyloxyphenoxy and 3-pentadecylphenoxy groups), a substituted or unsubstituted amino group having 1 to 30 carbon atoms (such as dimethylamino, diethylamino, n-hexylamino, cyclohexylamino and bis(2-cyanoethyl)amino groups), a substituted or unsubstituted amido groups having 1 to 30 carbon atoms (such as acetylamino, chloroacetylamino, trifluoroacetylamino, dodecenylsuccinimido, 2-hexadecenyl-3-carboxypropionylamino, pivaloylamino and 2-(2,4-di-t-pentylphenoxy)butyroxylamino groups), a substituted or unsubstituted sulfonamido group having 1 to 30 carbon atoms (such as benzenesulfonylamino, 4-chlorophenylsulfonylamino, N-methyl-4-methoxyphenylsufonylamino, methanesulfonylamino, n-octanesulfonylamino and 4-methylphenylsulfonylamino groups), a substituted or unsubstituted alkoxycarbonylamino group having 1 to 30 carbon atoms (such as ethoxycarbonylamino, ethoxycarbonyl-N-methylamino, N-ethylphenoxycarbonylamino, isobutyloxycarbonylamino and benzyloxycarbonylamino groups), a substituted or unsubstituted ureido group having 1 to 30 carbon atoms (such as 3,3-diethylureido, 3-cyclohexylureido, morpholinocarbonylamino, 3-(4-cyanophenyl)ureido, 3-n-octyl-1-methylureido and 1,3-diphenylureido groups), a substituted or unsubstituted carbamoyl group having 1 to 30 carbon atoms (such as methylcarbamoyl, ethylcarbamoyl, butylcarbamoyl, 4-methoxyphenylcarbamoyl, 3-(2,4-di-t-pentylphenoxy)propylcarbamoyl, pyrrolidinocarbonyl, hexadecylcarbamoyl and di-n-octylcarbamoyl groups), a substituted or unsubstituted alkoxycarbonyl group having 1 to 30 carbon atoms (such as methoxycarbonyl, ethoxycarbonyl, phenoxycarbonyl and hexadecyloxycarbonyl groups), a substituted or unsubstituted sulfamoyl group having 1 to 30 carbon atoms (such as methylfulfamoyl, diethylsulfamoyl, 3-(2,4-di-t-pentylphenoxy)-propylsulfamoyl, N-methyl-N-octadecylsulfamoyl, bis(2-methoxyethyl)sulfamoyl, 3-chlorophenylsulfamoyl and morpholinosulfonyl groups), a substituted or unsubstituted sulfonyl group having 1 to 30 carbon atoms (such as methanesulfonyl, propylsulfonyl, dodecylsulfonyl, 4-methylphenylsulfonyl, 2-ethoxy-5-t-butylphenylsulfonyl and 2-carboxyphenylsulfonyl groups), a cyano group, a halogen atom (such as fluorine, chlorine, bromine and iodine atoms), a substituted or unsubstituted acyl group having 1 to 30 carbon atoms (such as formyl, acetyl, trichloroacetyl, 2-phenoxypropionyl, benzoyl and 3-acetylaminobenzoyl), a carboxyl group, a sulfo group, a nitro group, a heterocyclic ring residual group having 1 to 30 carbon atoms (such as 1-tetrazolyl, 1,2,4-triazol-1-yl, 5-nitroindazol-1-yl, 5-methylbenzotriazol-1-yl and benzoxazol-2-yl groups), a sulfur residual group connected to a heterocyclic ring having 1 to 30 carbon atoms (such as 1-phenyltetrazol-5-ylthio, benzothiazol-2-ylthio and 6-methyl-1,3,3a,7-tetrazainden-4-ylthio groups), —PUG, or —Time—PUG.

Further, if possible, $R_{10}$ and $R_{20}$, and $R_{30}$ and $R_{40}$ may respectively bond to each other to form a saturated or unsaturated carbocyclic ring (provided that those which form a naphthalene ring together with the benzene ring of X are excluded) or a saturated or unsaturated heterocyclic ring. Examples are shown below.

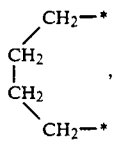

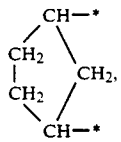

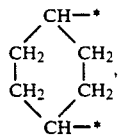

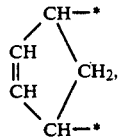

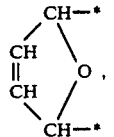

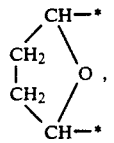

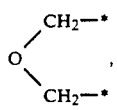

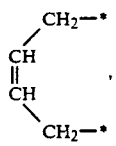

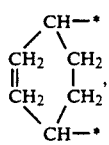

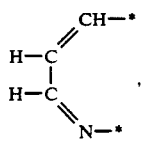

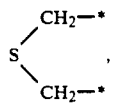

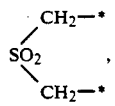

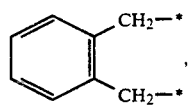

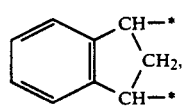

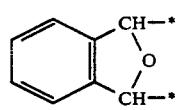

In the above formulas, * means a portion bonding as $R_1$, $R_2$, $R_3$, or $R_4$.

$R_{50}$ is a substituted or unsubstituted sulfonyl group having 1 to 30 carbon atoms (such as 4-methylphenylsulfonyl, methanesulfonyl, n-octylsulfonyl, 2-chloro-5-acetylaminophenylsulfonyl, 2-(2-methoxyethyl)-5-nitrophenylsulfonyl and 4-chlorophenylsulfonyl groups) or a substituted or unsubstituted acyl group having 1 to 30 carbon atoms (such as acetyl group, benzoyl group, 2-ethoxycarbonylbenzoyl, 4-nitrobenzoyl, chloroacetyl and 3,4-dimethoxybenzoyl groups), with the sulfonyl group being preferred. Further, in formulas (q), (r) and (s), R50's, when taken together, may form a ring.

EWG is an electron-withholding group having Hammett's $\sigma_{para}$ value exceeding 0.3 which bonds to $C_4$. Preferred examples are a substituted or unsubstituted carbamoyl group having 1 to 30 carbon atoms (such as methylcarbamoyl, ethylcarbamoyl, 4-methoxyphenylcarbamoyl, N-methyl-N-octadecylcarbamoyl, 3-(2,4-di-t-pentylphenoxy)propylcarbamoyl, pyrrolidinocarbonyl, hexadecylcarbamoyl and di-n-octylcarbamoyl groups), a substituted or unsubstituted sulfamoyl group having 1 to 30 carbon atoms (such as methylsulfamoyl, diethylsulfamoyl, 3-(2,4-di-t-pentylphenoxy)propylsulfamoyl, phenylsulfamoyl, pyrrolidinosulfamoyl and morpholinosulfamoyl groups), a substituted or unsubstituted alkoxycarbonyl group having 1 to 30 carbon atoms (such as methoxycarbonyl, ethoxycarbonyl, phenoxycarbonyl, 2-methoxyethoxycarbonyl and hexadecyloxycarbonyl groups), a substituted or unsubstituted sulfonyl group having 1 to 30 carbon atoms (such as methanesulfonyl, 4-methylphenylsulfonyl and dodecylsulfonyl groups), a substituted or unsubstituted acyl group having 1 to 30 carbon atoms (such as acetyl, hexanoyl, benzoyl and 4-chlorobenzoyl groups), a trifluoromethyl group, a carboxyl group, or a substituted or unsubstituted heterocyclic ring residual group having 1 to 30 carbon atoms (such as benzoxazol-2-yl and 5,5-dimethyl-2-oxazolin-2-yl groups), with the carbamoyl, alkoxycarbonyl and sulfamoyl groups being particularly preferred.

The amino group and hydroxyl group possessed by Q may respectively be protected by a protective group which can be deprotected in the development step. Examples of the protective group are an acyl group (such as acetyl, chloroacetyl, dichloroacetyl, benzoyl, 4-cyanobenzoyl and 4-oxopentanoyl groups), an alkoxycarbonyl group (such as ethoxycarbonyl, phenoxycarbonyl and 4-methoxybenzyloxycarbonyl groups), and an aminocarbonyl group (such as methylaminocarbonyl, 4-nitrophenylaminocarbonyl, 2-pyridylaminocarbonyl and 1-imidazolylcarbonyl groups), as well as those described in Japanese Patent Application (OPI) Nos. 197037/84 and 201057/84. If possible, the protective group may form a 5 to 7-membered ring together with $R_1$, $R_2$, $R_3$, $R_4$, or $R_5$, such as those described below.

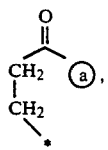

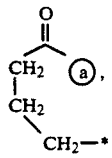

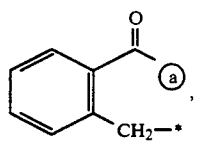

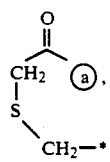

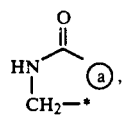

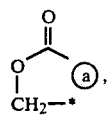

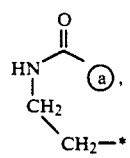

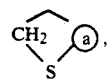

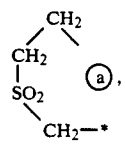

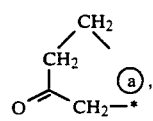

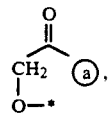

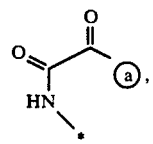

In the above formulas, (a) is bonded to the phenolic oxygen atom or the nitrogen atom of the amino group bonded to the aromatic ring, and * means a portion bonding as $R_{10}$, $R_{20}$, $R_{30}$, $R_{40}$, or $R_{50}$.

Exemplary compounds used in the present invention will next be shown, but these compounds are not to be construed as limiting the present invention in any manner.

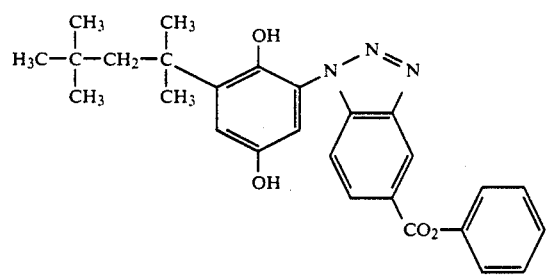
1
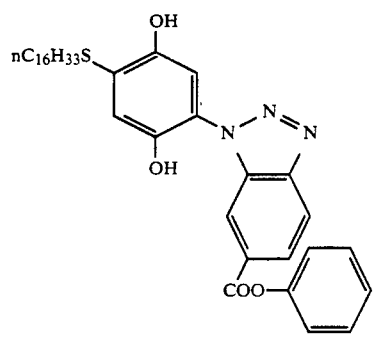
2
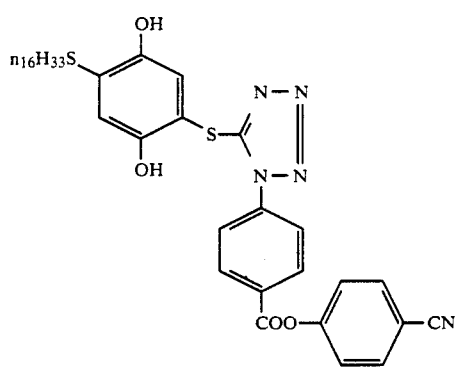
3
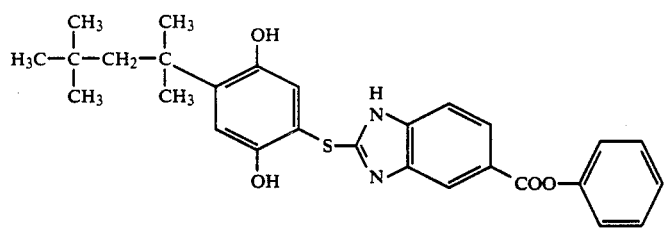
4
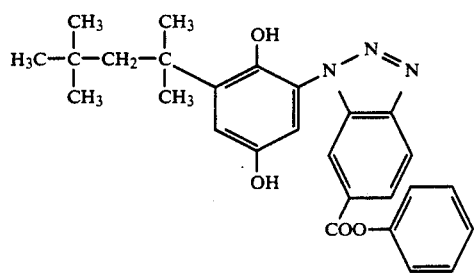
5

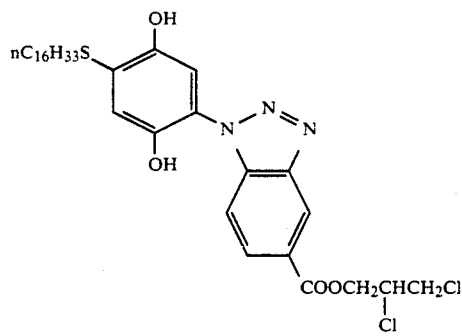
6
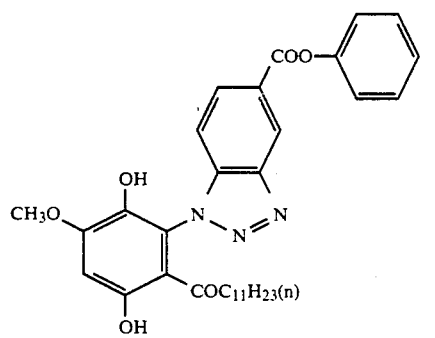
7
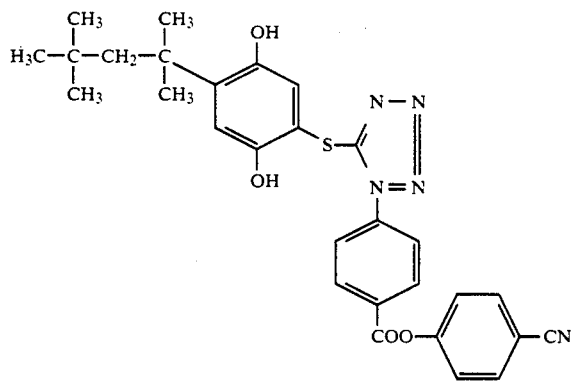
8
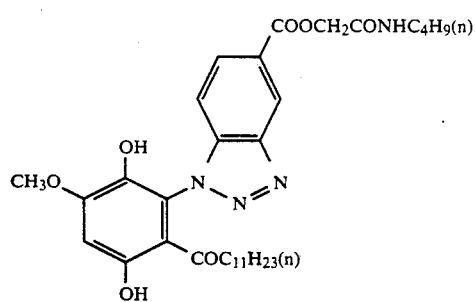
9
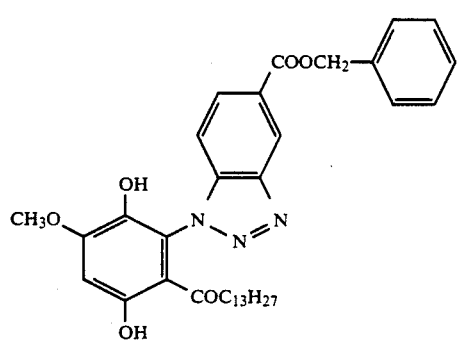
11

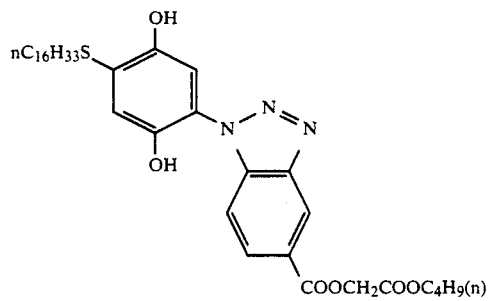
12
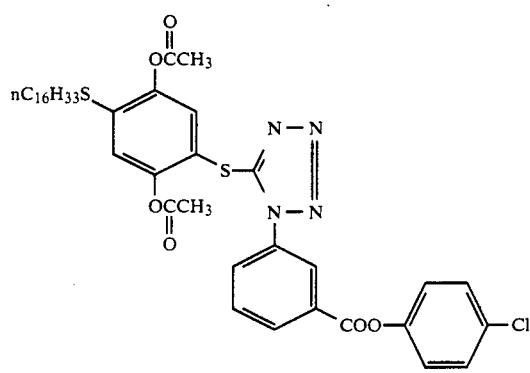
13
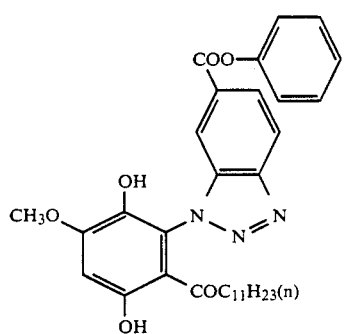
14
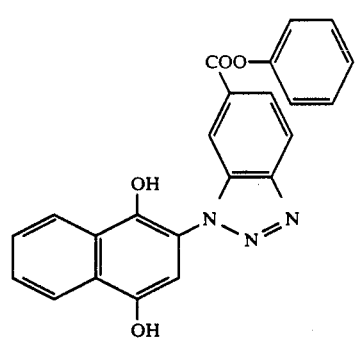
15
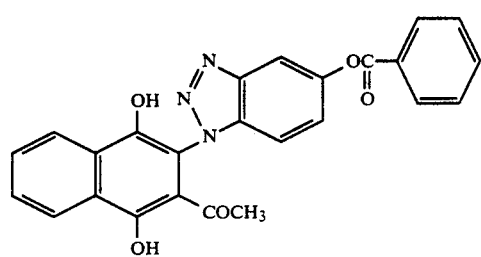
16

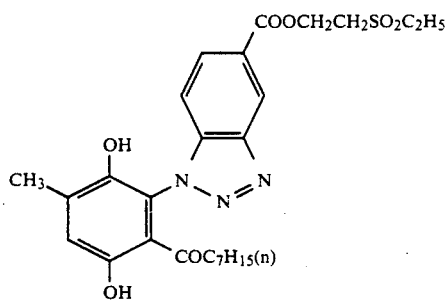
17
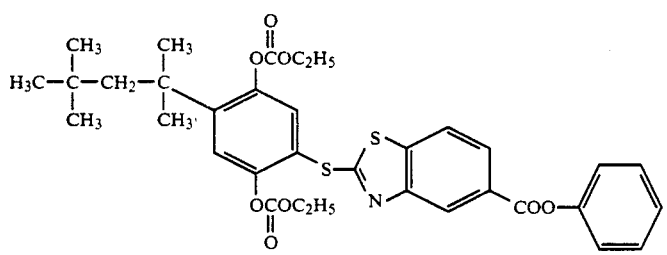
18
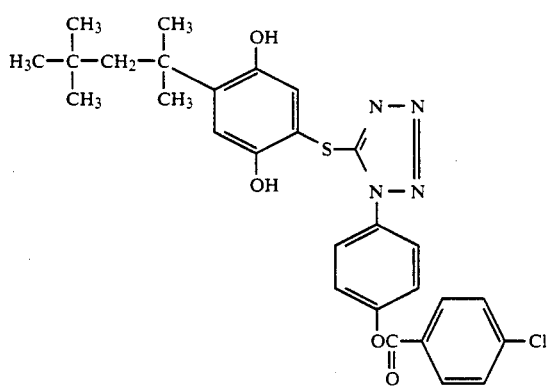
19
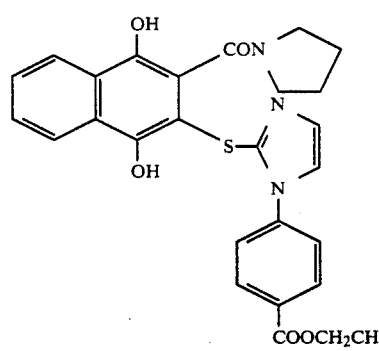
20
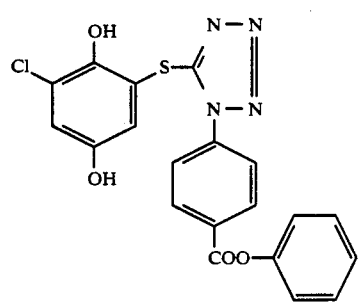
21

-continued
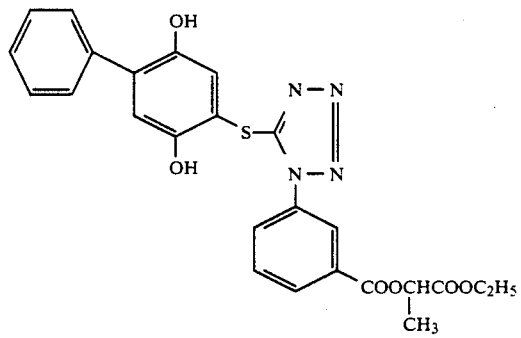
22
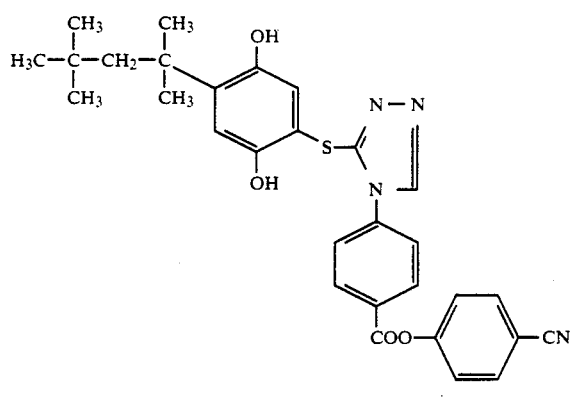
23
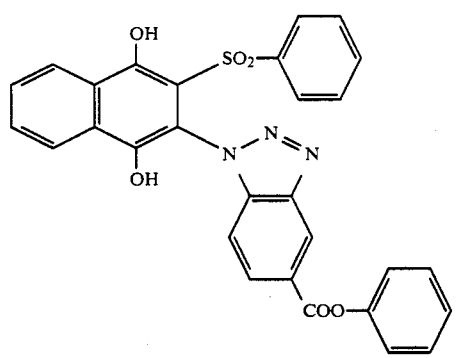
24
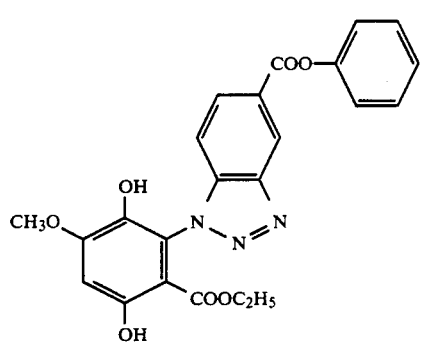
25

-continued
26
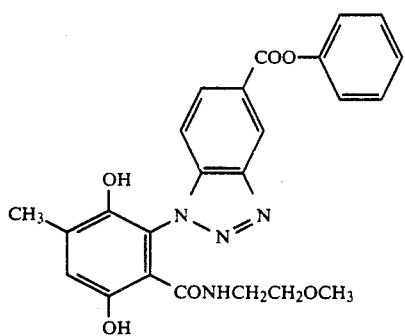
27
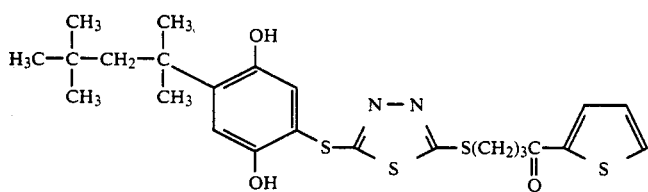
28
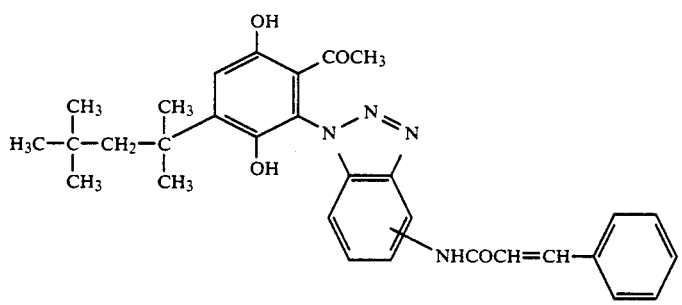
29
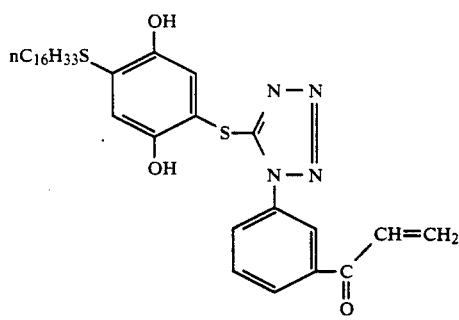
30
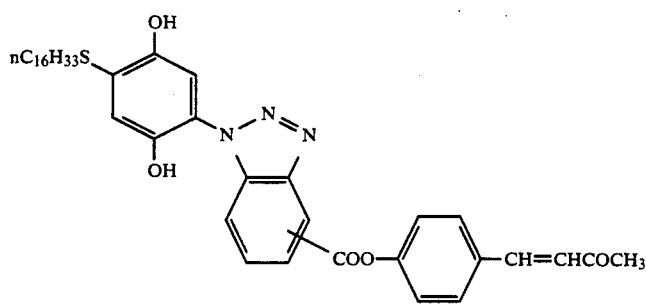

-continued
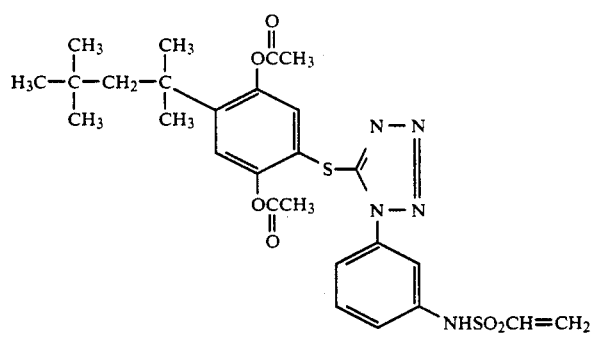
31
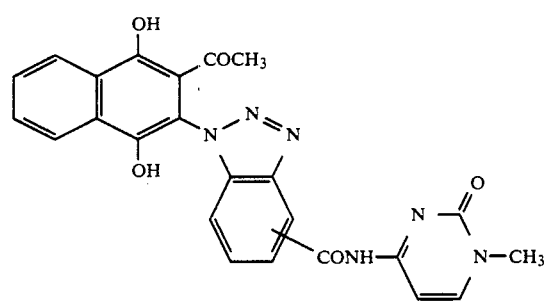
32
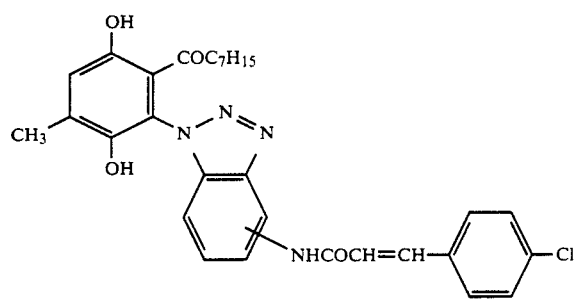
33
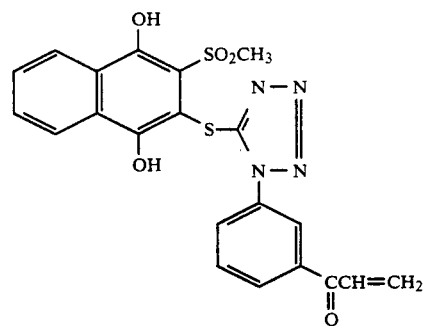
34
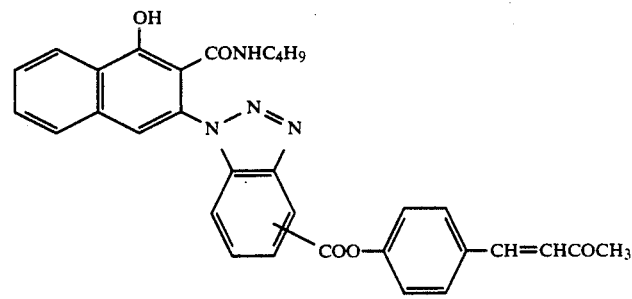
35

-continued
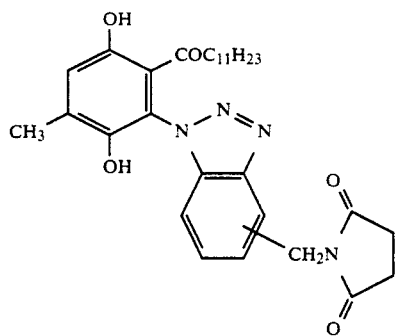 36
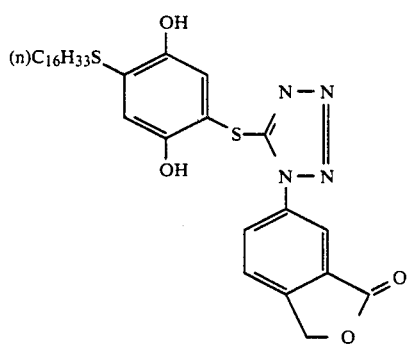 37
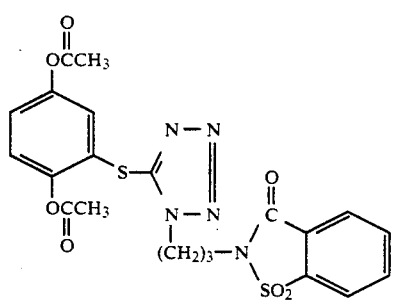 38
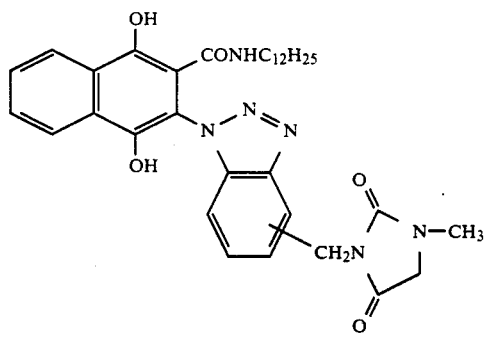 39
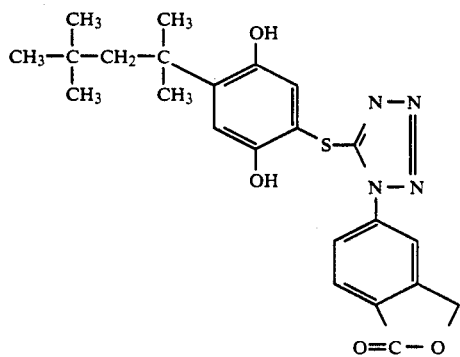 40

-continued
41
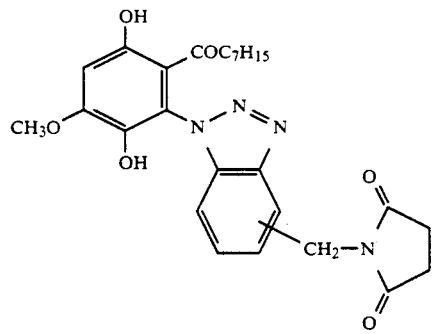
42
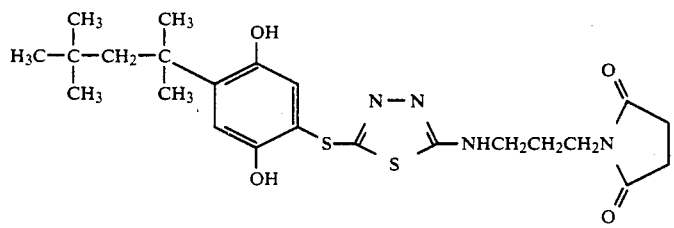
43
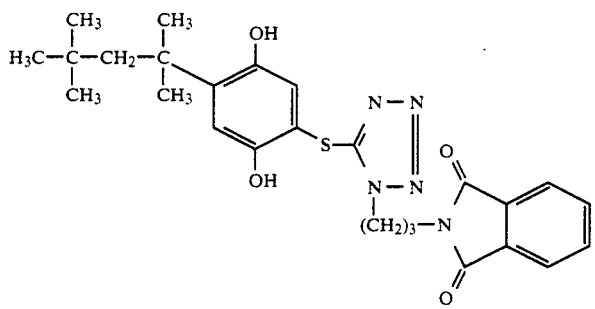
44
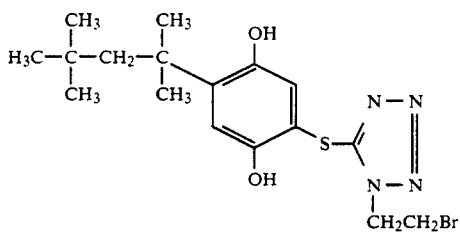
45
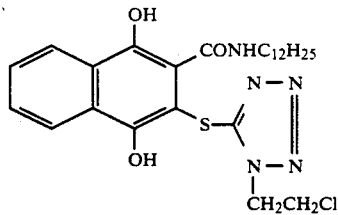
46
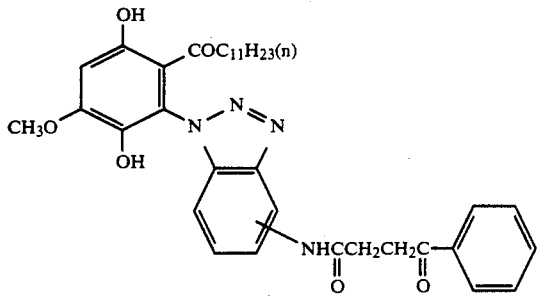

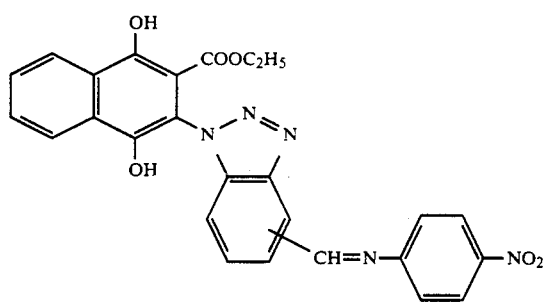
47
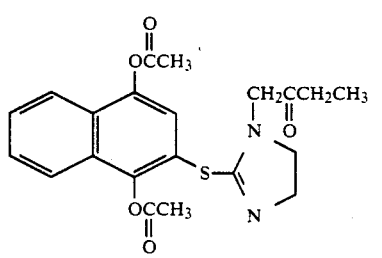
48
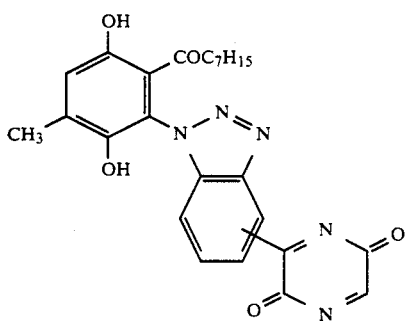
49
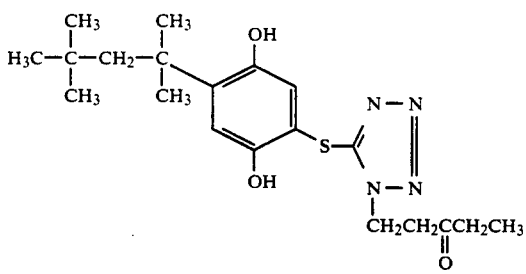
50
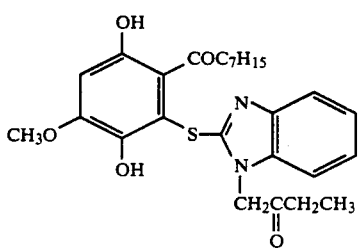
51

-continued
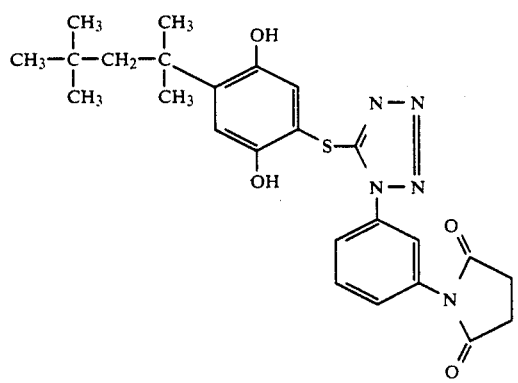
52
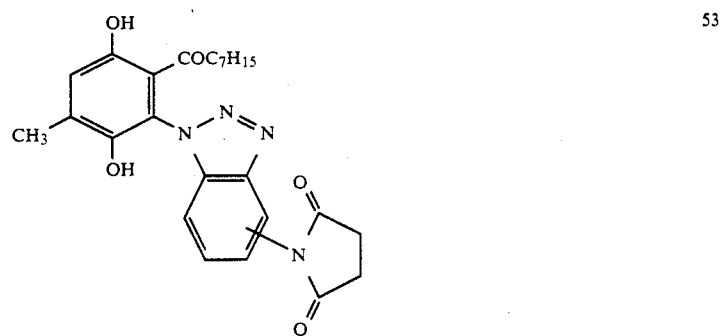
53
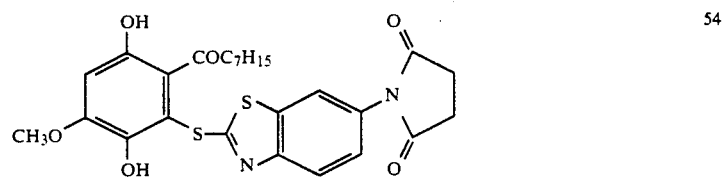
54
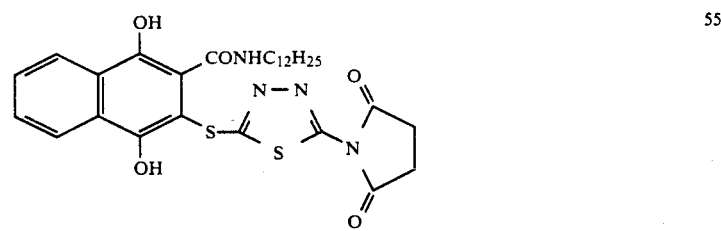
55
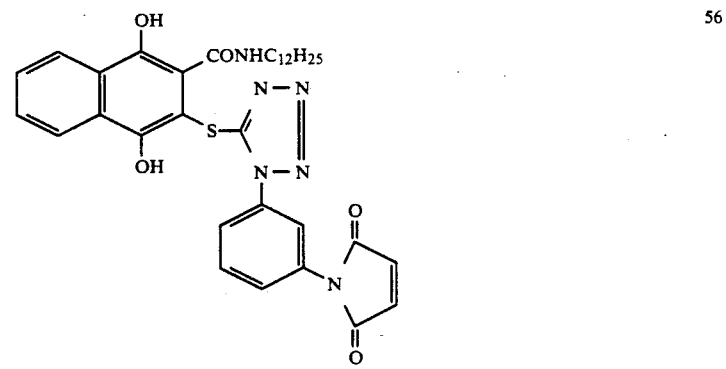
56

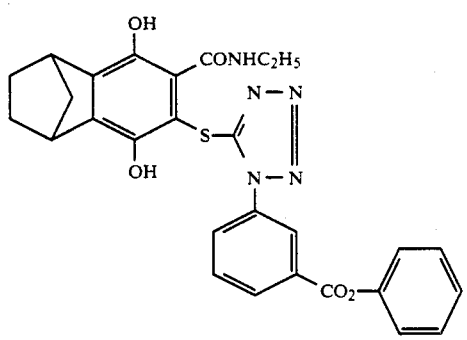
57
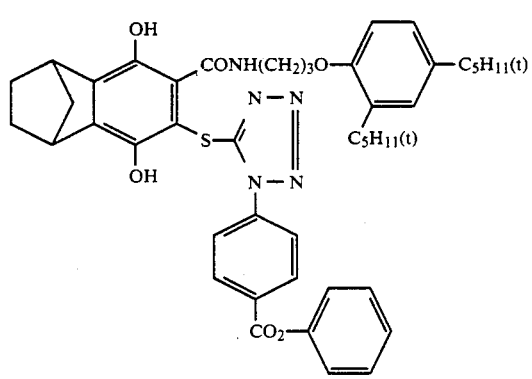
58
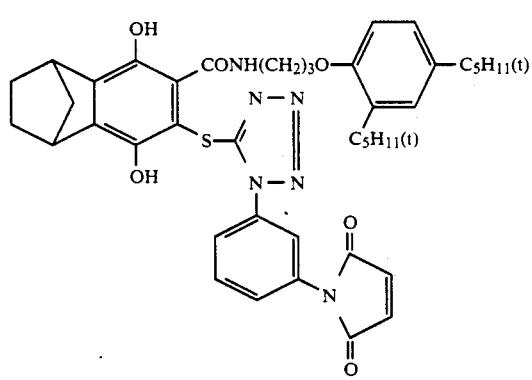
59
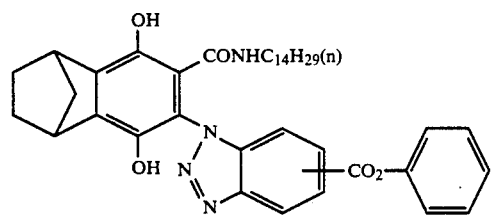
60
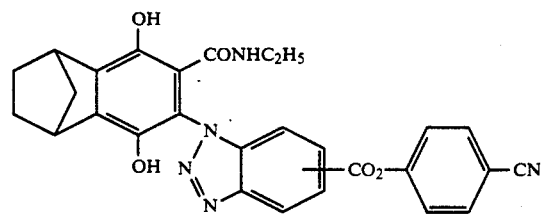
61

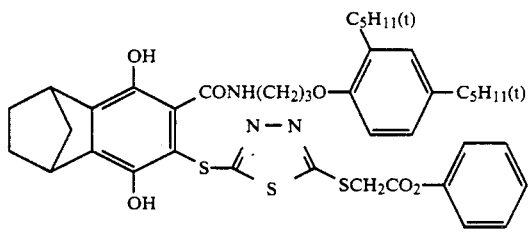
62
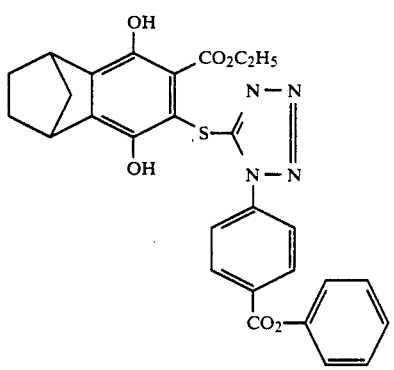
63
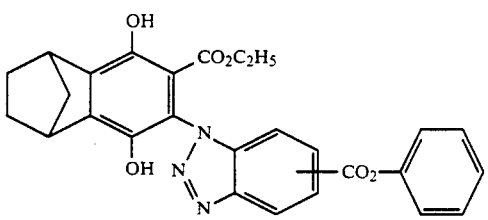
64
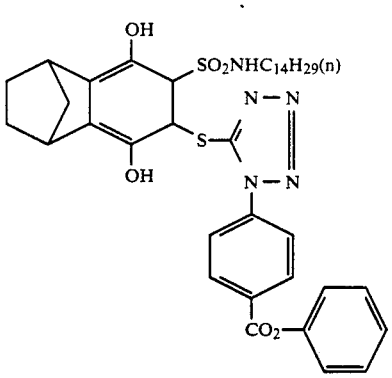
65
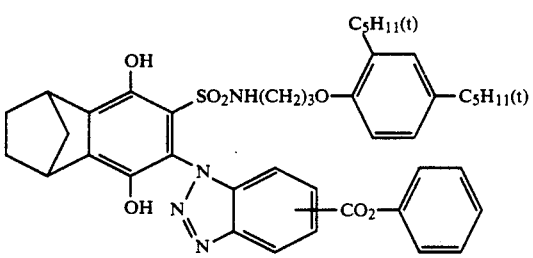
66

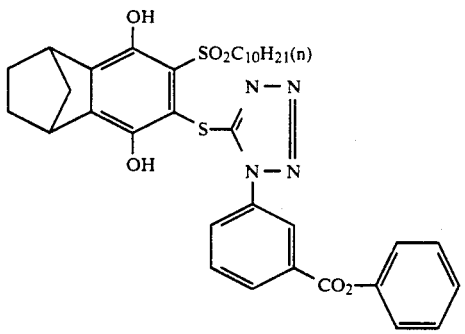
67
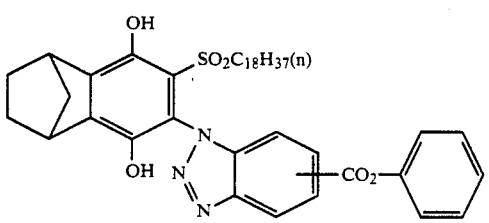
68
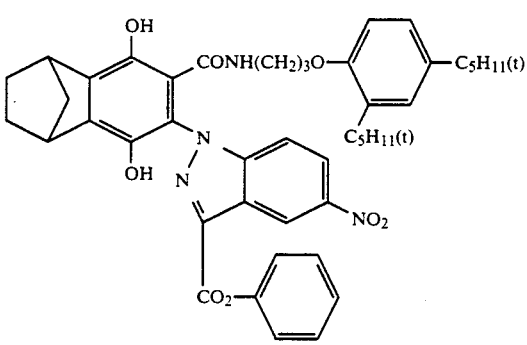
69
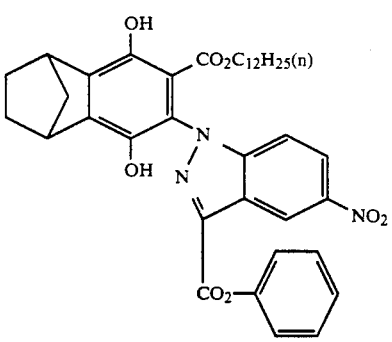
70
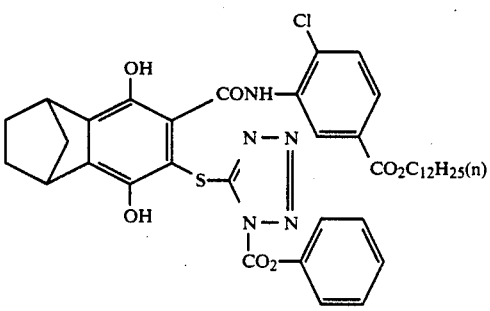
71

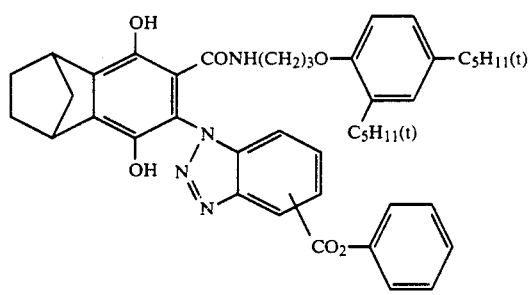
72
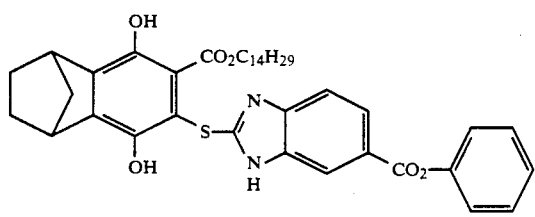
73
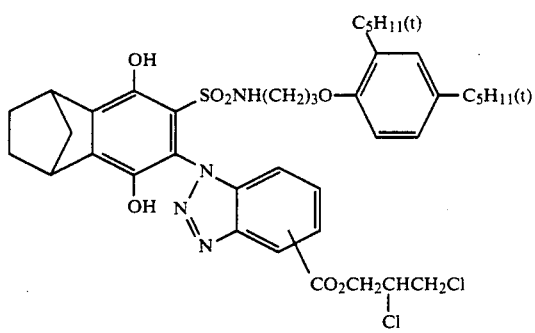
74
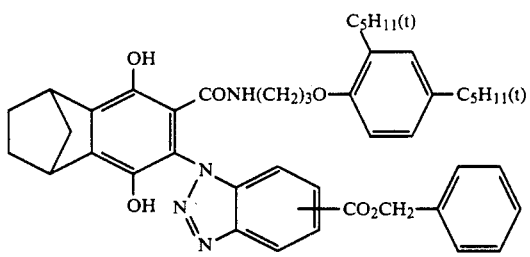
75
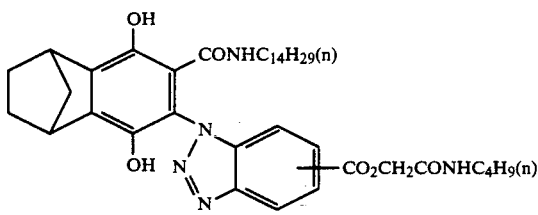
76
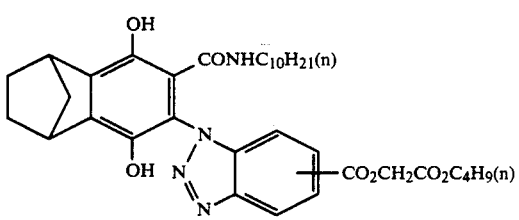
77

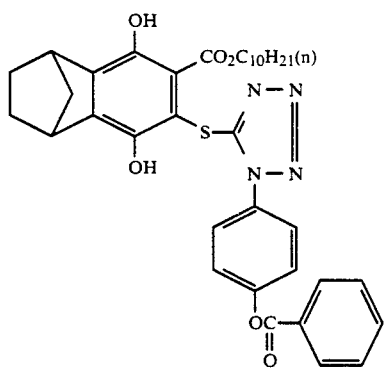
78
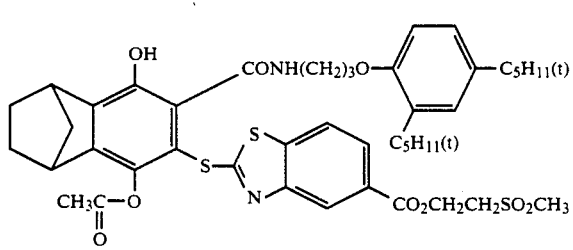
79
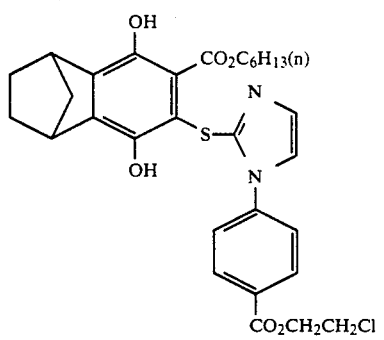
80
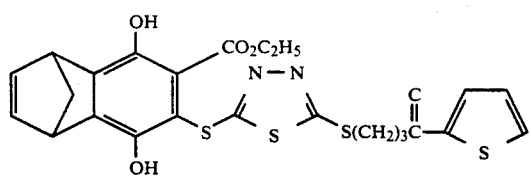
81
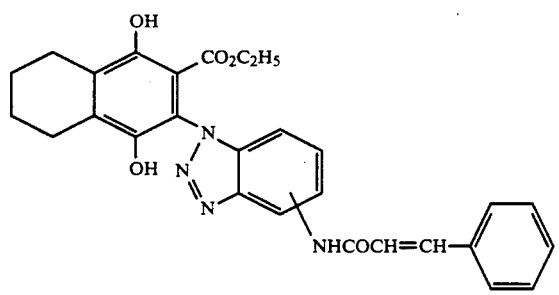
82

-continued
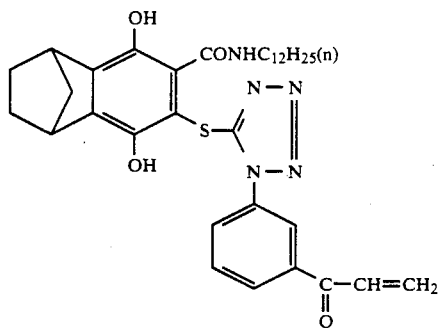
83
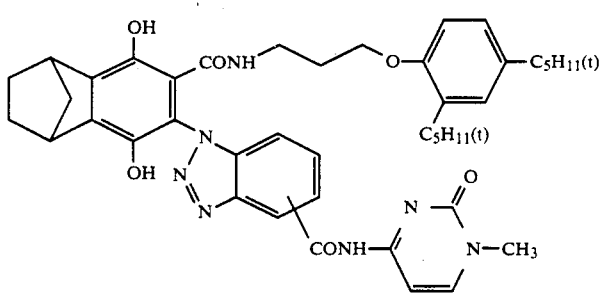
84
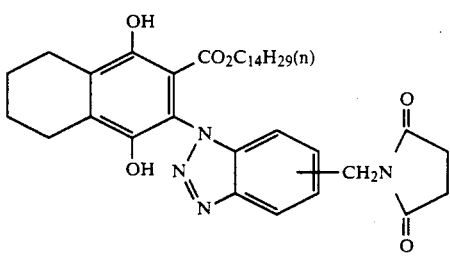
85
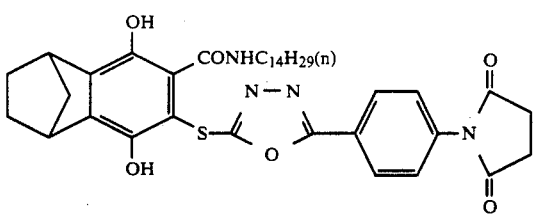
86
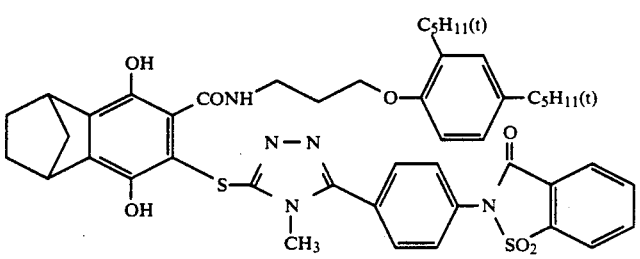
87

-continued
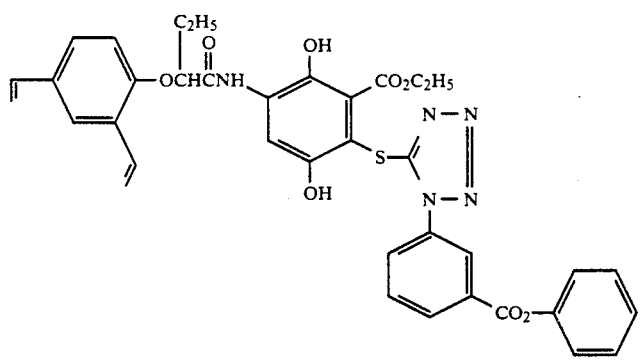
88
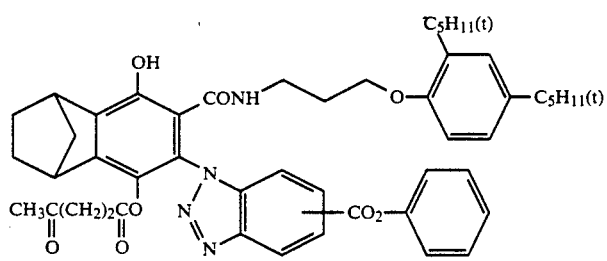
89
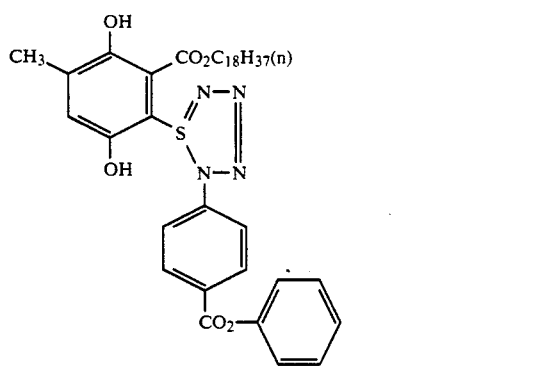
90
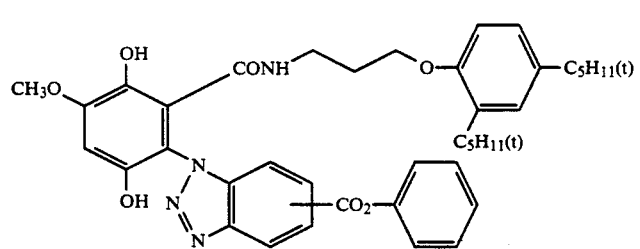
91
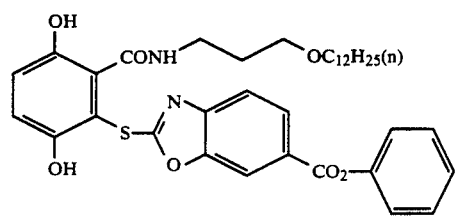
92

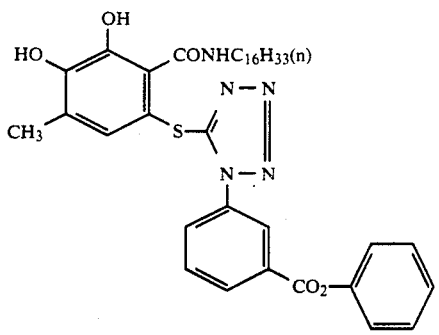
93
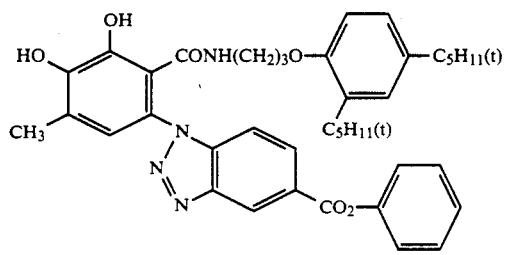
94
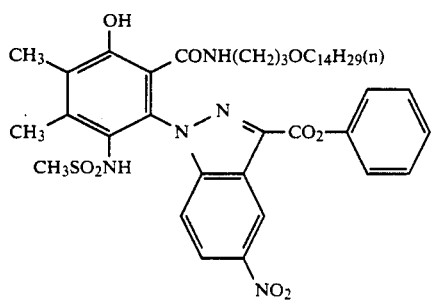
95
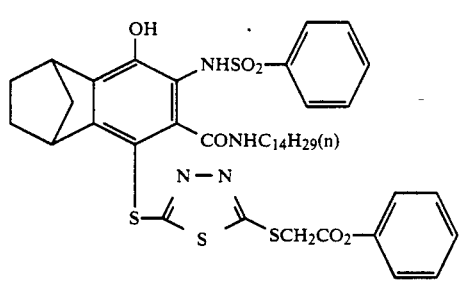
96
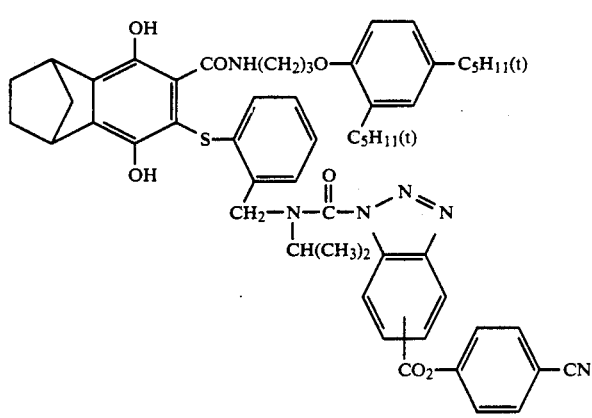
97

98

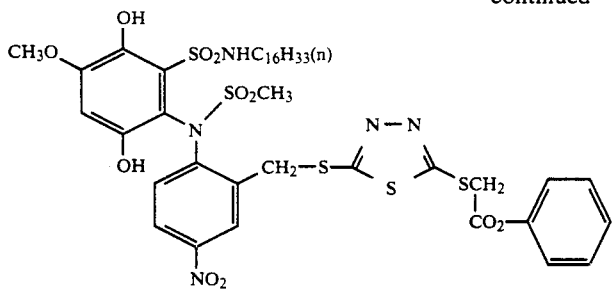

99

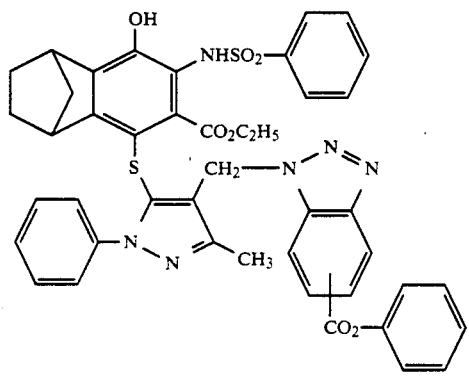

100

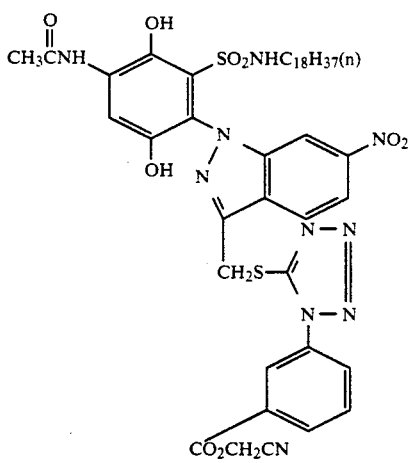

The compound shown by the formula (I) may generally be synthesized by the following two methods:

1) By reacting a benzoquinone derivative with a mercaptoazole or benzotriazole derivative in chloroform, 1,2-dichloroethane or carbon tetrachloride and in the presence of an acid catalyst such as p-toluenesulfonic acid, benzenesulfonic acid, trifluoromethanesulfonic acid or methanesulfonic acid at a temperature ranging from room temperature to 100° C.

2) By reacting a chlorine-, bromine- or iodine-substituted benzoquinone derivative with a photographically useful compound in a non-protonic polar solvent such as acetone, tetrahydrofuran and dimethylformamide and in the presence of a base such as potassium carbonate, sodium bicarbonate and sodium hydroxide at a temperature ranging from −20° C. to 100° C. to obtain a quinone form and reducing it with a reducing agent such as diethylhydroxylamine, sodium hydroxulfic and the like. (See *Research Disclosure* 18227 (1979), and *Liebigs Ann. Chem.*, 764, 131 (1972))

Specific examples of synthesizing the compounds of the present invention are shown below. The compounds used in the present invention can be easily synthesized by these methods.

SYNTHESIS EXAMPLE 1

Synthesis of Compound No. 1

After mixing tertiary octylbenzoquinone (20 g) and 5-phenoxycarbonylbenzotriazole (22 g) in acetonitrile (200 ml), a catalytic amount of p-toluenesulfonic acid was further added. The resulting mixture was refluxed under a nitrogen stream for about 8 hours. The solvent was concentrated and the residue was purified through the silica gel chromatography. A 4:1 mixture of hexane and ethyl acetate was used as the solvent. The first fraction was concentrated and the residue was crystallized from acetonitrile to obtain 4.3 g of Compound No. 1 (m.p.: 205°–207° C.).

SYNTHESIS EXAMPLE 2

Synthesis of Compound No. 3 p-benzoquinone (20 g) and 1-[4-(4-cyanophenoxycarbonyl)phenyl]-5-mercaptotetrazole (40 g) were mixed in acetonitrile (300 ml) and reacted at room temperature. The resultant crystals were filtered off and the obtained crystals were oxidized with manganese dioxide in acetone. The excess oxidizing agent was filtered off, the filtrate was concentrated, and the residue was crystallized from an aqueous acetone to obtain 20 g of a quinone form (m.p.; 173°-174 C). Twenty grams of this obtained quinone form and [n]hexadecylmercaptane (11 g) were mixed in acetonitrile (200 ml), and a catalytic amount of p-toluenesulfonic acid was further added and the resulting mixture was reacted at room temperature for 5 hours. The precipitated crystals were filtered off, the filtrate was concentrated and the residue was crystallized from acetonitrile to obtain 8 g of Compound No. 3. (m.p.: 98°-99° C.).

SYNTHESIS EXAMPLE 3

Synthesis of Compound No. 5

A mixture similar to that of Example 1 was prepared and p-toluenesulfonic acid was added. The resultant mixture was refluxed under a nitrogen stream for 3 hours. After the acetonitrile was concentrated, the residue was purified through silica gel chromatography. A 3:1 mixture of hexane and ethyl acetate was used as the solvent and the first small fraction was removed. The second fraction was concentrated and crystallized from acetonitrile to obtain 3.5 g of compound No. 5. (m.p.: 207°-209° C.)

SYNTHESIS EXAMPLE 4

Synthesis of Compounds Nos. 7 and 14

5-phenoxycarbonyl benzotriazole (20 g) was added to an acetonitrile solution of 5-methoxy-2-undecanoylbenzoquinone (15 g), and the resultant solution was stirred at room temperature for 2 hours. The resulting reaction mixture was dropwise added to an excess $Na_2S_2O_5$ solution and stirred for 1 hour. The obtained crystals were filtered and washed with water and crystallized from acetonitrile to obtain 3 g of the first compound (compound No. 7) (m.p. 162°-164° C.). Then the filtrate was left to stand in a refrigerator to obtain 2 g of Compound No. 14. (m.p. 130°-133° C.).

SYNTHESIS EXAMPLE 5

Synthesis of Compound No. 8

Tertiary octylbenzoquinone (10 g), 1-[4-(4-cyanophenoxycarbonylphenyl]-5-mercaptotetrazole (7 g) and a catalytic amount of p-toluenesulfonic acid were added to acetonitrile and the resulting mixture was reacted under a nitrogen stream at room temperature for 5 hours. The obtained crystals were filtered and the crystals were dissolved in ethyl acetate and then washed with water and separated. After the ethyl acetate layer was dried over anhydrous sodium sulfate and concentrated, the residue was recrystallized from acetonitrile to obtain 6.5 g of Compound No. 8. (m.p.: 199°-200° C.).

SYNTHESIS EXAMPLE 6

Synthesis of Compound No. 34

(1) Synthesis of 2-phenylsulfonyl-1,4-dihydroxynaphthalene 1,4-naphthoquinone (15.8 g) was dissolved in 100 ml of a mixture of ethyl acetate and acetic acid (9:1) and sodium benzenesulfinate (24.6 g) was added. The resulting mixture was stirred for 5 hours and the obtained crystals were filtered and washed with a small amount of acetone. (Yield: 22.5 g)

(2) Synthesis of 2-phenylsulfonyl-1,4-naphthoquinone

The above-identified naphthohydroquinone (10 g) was suspended in acetone (150 ml) and manganese dioxide was added to this solution in excess and refluxed for 3 hours. Inorganic substances were removed by filtration while hot and the solvent was distilled off to obtain crystals of a naphthoquinone form. (Yield: 4.5 g)

(3) 2-sulfophenyl-3-{1-(3-acryloylphenyl)tetrazole-5-yrthio}-1,4-dihydroxynaphthalene (Compound No. 34)

The above-identified naphthoquinone form (4 g) and 1-(3-acryloylphenyl)-5-mercaptotetrazole (3 g) were suspended in ethyl acetate (80 ml) and refluxed under heating for 4 hours. After removal of impurities, the remaining solution was cooled and the produced crystals were filtered off. (Yield: 2 g, m.p.: 205°-208° C.) (decomposed)

SYNTHESIS EXAMPLE 7

Synthesis of Compound No. 36

2-methyl-5-lauroylbenzoquinone (5 g) and 5-succinimidobenzotriazole (3 g) were refluxed under heating in acetonitrile (60 ml). After cooling the reaction mixture, the produced crystals were filtered off. (Yield: 2 g, m.p.: 196°-199° C.)

SYNTHESIS EXAMPLE 8

Synthesis of Compound No. 45

(1) Synthesis of 2-laurylcarbamoyl-1,4-dihydroxynaphthalene 2-phenoxycarbonyl-1,4-dihydroxynaphthalene (28 g) was suspended in acetonitrile (150 ml) and laurylamine (22.2 g) was dropwise added. The resulting mixture was refluxed for 4 hours. After completion of the reaction, the reaction mixture was cooled and the produced crystals were filtered off. (Yield: 26.8 g)

(2) Synthesis of 3-chloro-2-laurylcarbamoyl-1,4-naphthoquinone

The above-identified naphthohydroquinone (7.4 g) was added to chloroform (100 ml) and stirred. Sulfuryl chloride (5.7 g) was gradually added dropwise to the mixture while keeping it at 5° to 10° C. After completion of the reaction, water was added and the resulting solution was separated. The chloroform solution was removed, and after distilling-off of the solvent, the remaining mixture was quickly purified through a column chromatography using silica gel. (Yield: 3.4 g)

(3) Synthesis of 2-laurylcarbamoyl-3-{1-(2-chloroethyl)-5-yrthio}1,4-naphthoquinone Four grams of the crystals obtained in (2) were dissolved in acetone (70 ml) and the resulting solution was cooled to 5° C. with iced water. 1-(2-chloroethyl)-5-mercaptotetrazole (1.8 g) was added to the above solution and anhydrous potassium carbonate (1.7 g) was further added to the mixture and stirred for 3 hours. The produced crystals were filtered off. In order to remove inorganic substances, the crystals were washed with an aqueous 10% acetic acid (200 ml) and dried. (Yield: 3.5 g)

(4) Synthesis of 2-laurylcarbamoyl-3-{1-(2-chloroethyltetrazole)-5-yrthio}1,4-dihydroxynaphthalene (Compound No. 45)

Sodium hydrosulfite (8.7 g) was dissolved in water (80 ml) and an acetonitrile solution of the naphthoquinone form obtained in (3) (5.5 g) was added to the solution at room temperature. Crystals formed quickly and these crystals were filtered off and recrystallized from ethyl acetate. (Yield: 3.8 g, m.p.: 177°–181° C.)

SYNTHESIS EXAMPLE 9

Synthesis of Compound No. 46

2-methoxy-5-lauroylbenzoquinone (7g) and 5-(3-benzoylpropioneamido)benzotriazole (4.5 g) were mixed in acetonitrile (240 ml) and refluxed under heating for 2.5 hours. Undissolved substances were filtered off and the remaining solution was cooled to obtain crystals by filtration. (Yield: 1.7 g, m.p.: 188°–192° C.) (decomposed).

SYNTHESIS EXAMPLE 10

Synthesis of Compound No. 58

(1) Synthesis of 3,6-dihydroxybenzonorbornene-4-carboxylic acid 3,6-Dihydroxybenzonorbornene (81.8 g), potassium carbonate (260 g) and dimethylformamide (400 ml) were mixed and reacted in an autoclave at 180° C. for 8 hours while bringing into contact with carbon dioxide at 50 kg/cm$^2$.

After cooling, water was added to the reaction mixture and then rendered acidic by hydrochloric acid, followed by extracting with ethyl acetate. The organic layer was washed with water, and the ethyl acetate was distilled off under a reduced pressure. Warm water was added to the residue, and the mixture was stirred. There were thus obtained crystals of 3,6-dihydroxybenzonorbornene-4-carboxylic acid. (Yield 92.1 g (90.2 %))

(2) Synthesis of phenyl 3,6-dihydroxybenzonorbornene-4-carboxylate

According to the method described in Japanese Patent Application (OPI) No. 28139/78, a phenyl ester (oil) was obtained from 3,6-dihydroxybenzonorbornene-4-carboxylic acid.

(3) Synthesis of 3,6-dihydroxy-4-[3-(2,4-di-t-pentylphenoxy)propylcarbamoyl]benzonorbornene The phenyl ester (14.8 g) synthesized in (2) above was mixed with 3-(2,4-di-t-pentylphenoxy)propylamine (14.6 g), and the mixture was reacted at 140° C. under a reduced pressure of 20 mmHg for 4 hours. After cooling, the reaction product was crystallized from n-hexane to obtain 3,6-dihydroxy-4-[3-(2,4-di-t-pentylphenoxy)propylcarbamoyl]benzonorbornene. (Yield: 15.1 g (61.2 %), m.p.: 142° C.)

(4) Synthesis of 3,6-dioxo-4-[3-(2,4-di-t-pentylphenoxy)propylcarbamoyl]-5-chlorobenzonorbornene The above (4.9 g) synthesized in (3) above was dissolved in tetrahydrofuran (60 ml), and N-chlorosuccinimide (2.9 g) was added thereto, followed by reacting the reaction for 6 hours. Thereafter, the solvent was distilled off, and the residue was purified by silica gel chromatography to obtain 3,6-dioxo-4-[3-(2,4-di-t-pentylphenoxy)propylcarbamoyl]-5-chlorobenzonorbornene. (Yield: 5.0 g (95.7 %).

(5) Synthesis of Compound No. 58

1-(4-Phenoxycarbonylphenyl)-5-mercaptotetrazole (5.1 g) and potassium carbonate (3.6 g) were mixed with acetone (70 ml), and the mixture was stirred for 30 minutes. Thereafter, 3,6-dioxo-4-[3-(2,4-di-t-pentylphenoxy)propylcarbamoyl]-5-chlorobenzonorbornene (9.0 g) was added thereto, followed by reacting for 2 hours. Inorganic matters were filtered out, the actone was distilled off under reduced pressure, and the residue was dissolved in ethyl acetate. A 27% sodium hydrosulfite solution (100 ml) was then added thereto, followed by vigorously stirring. After 10 minutes, the reaction mixture was subjected to liquid separation, and the organic layer was washed with water twice and then with saturated salt water one time, followed by drying over anhydrous sodium sulfate. The resulting solution was filtered, the sodium sulfate was removed, the ethyl acetate was distilled off, and the residue was crystallized from n-hexane. (Yield: 13.0 g (96.2%), m.p.: 162°–165° C.)

SYNTHESIS EXAMPLE 11

Synthesis of Compound No. 72

3,6-Dioxo-4-[3-(2,4-di-t-pentylphenoxy)propylcarbamoyl]-5-chlorobenzonorbornene (5.3 g) was dissolved in acetone (50 ml). Potassium carbonate (2.0 g) and 5-phenoxycarbonylbenzotriazole (2.4 g) were added thereto, followed by reacting at 10° C. or lower for 5 hours. Thereafter, inorganic matters were filtered out, the acetone was distilled off, and the residue was dissolved in ethyl acetate (80 ml). A 27% sodium hydrosulfite solution (70 ml) was then added thereto, followed by vigorously stirring. After 10 minutes, the reaction mixture was subjected to liquid separation, and the organic layer was washed with water twice and then with saturated salt water one time, followed by drying over anhydrous sodium sulfate. The resulting solution was filtered, the sodium sulfate was removed, and the ethyl acetate was distilled off. The residue was carefully purified by silica gel chromatography using an n-hexane/ethyl acetate mixed solvent. Fractions of the object compounds were gathered and crystallized from acetonitrile. (Yield: 5.2 g (71%), m.p.: 156°–159° C.)

The novel photographic DIR compound of the present invention is believed to be cross-oxidized by redox reaction with the oxidized product of the developing agent formed in an image-wise pattern during development, as are the DIR hydroquinones described in U.S. Pat. No. 3,379,529 and the like, and releases a development restraining substance in an image-wise pattern and is converted into a colorless oxidized product. The development restraining substance released in an image-wise pattern restrains development in an image-wise pattern and shows DIR effects such as fine-grain images, softening of the color tone, improved sharpness of the image, better color reproduction and the like. The DIR compound of the present invention is extremely active and by even a small addition of it, produces surprisingly good effects as compared with the conventional DIR hydroquinones, as discussed later on.

The photographic DIR compound of the present invention may be used equally for a photographic material for monochrome development as well as for color image forming materials. The amounts to be used are not particularly limited, but preferably $10^{-6}$ to 1 mol/-mol Ag, and particularly preferably $10^{-5}$ to $10^{-1}$ mol/-mol Ag are usually used.

The photographic DIR compound of the present invention may be introduced into a photographic layer by dispersion by the known method which will be described later on. In this case, the photographic DIR compound of the present invention may be used singly or in combination of two or more different compounds. The photographic DIR compound of the present invention may also be used together with a coupler and added to the same emulsion layer as the coupler, or it may be added as a separate emulsified dispersion to a photographic auxiliary layer such as the intermediate layer.

When using the present compound in accordance with the present invention or when using a coupler together with the present invention (the coupler will be described later on), the known method such as the one described in U.S. Pat. No. 2,322,027 is used by introducing the compound into the silver halide emulsion layer. For example, the present compound is dissolved in the following solvents and dispersed into a hydrophilic colloid:

Alkyl phthalate (e.g., dibutyl phthalate and dioctyl phthalate), phosphate (e.g., diphenyl phosphate, triphenyl phosphate, tricresyl phosphate and dioctylbutyl phosphate), citrate (tributylacetyl citrate), benzoate (e.g., octyl benzoate), alkylamide (diethyllaurylamide), aliphatic acid esters (e.g., dibutoxyethyl succinate and diethyl azelate), trimesate (e.g., tributyl trimesate); or an organic solvent having a boiling point of 30° C. to 150° C., such as lower alkyl acetates such as ethyl acetate and butyl acetate, ethyl propionate, secondary butyl alcohol, methylisobutylketone, $\beta$-ethoxyethyl acetate and methyl cellosolve acetate.

The above-illustrated high boiling point organic solvents and low boiling point organic solvents may be used in combination.

Further, the dispersion method employing the polymers described in Japanese Patent Application Publication No. 39,853/76 and Japanese Patent Application (OPI) No. 59,943/76 may also be used.

When the coupler contains an acid radical such as carboxylic acid and sulfonic acid, the present compound is introduced into a hydrophilic colloid as an aqueous alkaline solution.

Gelatin is advantageously used for the binder or protection colloid which may be used for the emulsion layer or middle layer of the photographic material of the present invention, but other hydrophilic colloids may also be employed singly or in combination with gelatin.

In accordance with the present invention, the gelatin may be treated with lime or an acid. The details of preparing gelatin are described in "The Macromolecular Chemistry of Gelatin" by Arthur Weiss (Academic Press, 1964).

The above-identified hydrophilic colloids which may be employed in the present invention include proteins such as a gelatin derivative, a graft polymer of a gelatin with other high polymers, albumin and casein; cellulose derivatives such as hydroxyethyl cellulose, carboxymethyl cellulose and cellulose sulfate, sugar derivatives such as sodium alginate and starch derivatives; and various synthetic hydrophilic polymer materials including homo- and copolymers such as polyvinyl alcohol, polyvinyl alcohol partially substituted by acetyl, poly-N-vinyl pyrrolidone, polyacrylic acid, polymethacrylic acid, polyacrylamide, polyvinylimidazole and polyvinylpyrazole.

As the silver halide used for the photographic emulsion layer of the photographic material employed in the present invention, any one chosen from the group consisting of silver bromide, silver iodobromide, silver iodochlorobromide, silver chlorobromide and silver chloride may be used. The preferred silver halide is silver iodobromide containing not greater than 15 mol % silver iodide.

The average size of the silver halide grains contained in the photographic emulsion is not particularly limited by preferably does not exceed 3 $\mu$ (the grain size is expressed in terms of the projected area, using as the grain size the diameter of a spherical or approximately spherical grain or the length of one edge of a cubic grain).

The grain size distribution may be either broad or narrow.

The morphology of the silver halide grains contained in the photographic emulsion may be regular such as cubes or octahedrons or may be anomalous such as spheres or tables or even a combination of these. The grains may consist of a mixture or two or more of these different morphologies A emulsion may be used where "super-tabular" silver halide grains having a diameter at least five times their thickness account for not less than 50% of the total projected areas.

The silver halide grains may have a surface layer whose phase is different from that of the interior. The latent images may be formed primarily on the surface of the grains or inside of them.

The photographic emulsion used in accordance with the present invention may be prepared by the methods described in "Chimie et Physique Photographique" by P. Glafkides (published by Paul Montel, 1967), "Photographic Emulsion Chemistry" by G. F. Duffin (published by the Focal Press, 1966), "Making and Coating Photographic Emulsion" by V. L. Zelikman et al (published by The Focal Press, 1964) and other literature. In other words, the acid method, neutral method, ammonia method may all be used alike, and for reacting a soluble silver salt with a soluble halogen salt, the single jet method and the double jet method can be used either singly or in combination.

A method comprising forming grains in excess silver ion (the so-called reverse single jet method) may also be employed.

As one type of the double jet method, the method involving maintaining at a constant level pAg in the liquid phase wherein a silver halide is produced, i.e., the so-called controlled double jet method may be used. According to this method, the obtained silver halide emulsion has a regular crystal form and its grain size is approximately uniform.

It is also possible to use a mixture of 2 or more different silver halide emulsions prepared separately.

A cadmium salt, zinc salt, lead salt, thallium salt, iridium salt or a complex salt thereof, a rhodium salt or its complex salt, iron salt or iron complex salt may be present during the silver halide grain forming process or the physical maturing of the produced grains.

The silver halide emulsion is usually chemically sensitized. For chemical sensitization, for example, the method described in pages 675-734 of "Die Grundlagen der Photographischen Prozesse mit Silberhalogeniden" edited by H. Frieser (Akademiische Verlagsgesellschaft, 1968) may be employed.

Specifically, the sulfur-sensitization employing a compound which may react with active gelatin or silver (e.g., a thiosulfate salt, thiourea, mercapto compounds and Rhodamines); the reduction sensitization employing a reducing substance (e.g., stannous salts, amines, hydrazine derivatives, formamidinesulfinate and silane compounds); and the noble metal sensitization employing noble metal compounds (e.g., complex salts, of gold and of the metals belonging to the VIII group of the Periodic Table, such as Pt, Ir and Pd). These methods may be used either singly or in combination.

Various compounds may be incorporated in the photographic emulsion used in accordance with the present invention for the purpose of preventing fog in the preparation and storage of the sensitive material or in the photographic processing or for stabilizing the photographic performance. Specifically, the following various compounds known as anti-foggants of stabilizers can be incorporated:

Azoles such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (particularly 1-phenyl-5-mercaptotetrazole); mercaptopyrimidines; mercaptotriazines; thioketo compounds such as oxazolinethione; azaindenes such as triazaindenes, tetraazaindenes (particularly 4-hydroxy-substituted (1, 3, 3a, 7) tetraazaindenes) and pentaazaindenes; benzenethiosulfonic acid, benzenesulfinic acid, benzenesulfonic acid amides and the like.

The photographic emulsion layer of the sensitive material prepared in accordance with the present invention or other hydrophilic colloid layers may contain various surfactants as coating aids or antistatic agents or for providing better slip, emulsified dispersion, adhesion prevention and improved photographic properties (e.g., development acceleration, higher contrasting and sensitization).

Exemplary surfactants include the following:

nonionic surfactants such as saponin (steroid saponin), alkylene oxide derivatives (e.g., polyethylene glycol, polyethylene glycol/polyethylene glycol condensation products, polyethylene glycol alkyl ethers or polyethylene glycol alkylaryl ethers, polethylene glycol esters, polyethylene glycol sorbitan esters, polyalkylene glycol alkylamines or polyalkylene glycol alkylamides and polyethylene oxide adducts of silicone), glycidol derivatives (e.g., alkenylsuccinic acid polyglycerides and alkylphenol polyglycerides), aliphatic acid esters of polyhydroxy alcohol and alkyl esters of sugar; anionic surfactants containing acid groups such as carboxy, sulfo and phospho groups, sulfate ester groups and phosphate ester groups, such as alkylcarboxylic acid salts, alkylsulfonic acid salts, alkylbenzenesulfonic acid salts, alkylnaphthalenesulfonic acid salts, alkylsulfate esters, alkylphosphate esters, N-acyl-N-alkyltaurines, sulfosuccinate esters, sulfoalkylpolyoxyethylenealkylphenyl ethers and polyoxyethylene alkylphosphate esters; ampholytic surface active agents such as amino acids, aminoalkylsulfonic acids, aminoalkylsulfate esters or aminoalkylphosphate esters, alkyl betaines and amine oxides; and cationic surfactants such as alkylamine salts, aliphatic or aromatic quaternary ammonium salts, heterocyclic quaternary ammonium salts such as pyridinium and imidazolium, and aliphatic or heterocycle-containing phosphonium or sulfonium salts.

In order to improve sensitivity, and contrast or to accelerate development, it is also possible to incorporate in the photographic emulsion layer of the sensitive material of the present invention, for example, polyalkylene oxides or their derivatives such as ethers, esters and amines, thioether compounds, thiomorpholines, quaternary ammonium salt compounds, urethane derivatives, urea derivatives, imidazole derivatives, 3-pyrazolidones and the like.

In order to improve dimensional stability and other properties, a dispersion of a synthetic polymer which does not or which hardly dissolve in water may be incorporated in the photographic emulsion layer or other hydrophilic colloid layers of the photographic material of the present invention. For example, polymers which contain as the monomeric ingredient the following substances either singly or in combination may be used:

Alkyl (meth)acrylate, alkoxyalkyl (meth)acrylate, glycidyl (meth)acrylate, (meth)acrylamide, vinyl esters (e.g. vinyl acetate), acrylonitrile, olefin and styrene. Further, these may be used in combination with acrylic acid, methacrylic acid, $\alpha,\beta$-unsaturated dicarboxylic acid, hydroxyalkyl (meth)acrylate, sulfoalkyl (meth)acrylate, styrene sulfonic acid and the like.

The photographic emulsion used in accordance with the present invention may be spectrally sensitized with methine dyes and the like. Exemplary dyes used in the present invention include cyanine, merocyanine, complex merocyanine, horopolar cyanine, hemicyanine, styryl and hemioxonol dyes. Particularly useful dyes are cyanine and merocyanine dyes and those dyes which belong to the group of complex merocyanine dyes. Any one of the nuclei generally used for cyanine dyes as basic heterocyclic nuclei is applicable for the above-illustrated dyes. Specifically, pyrroline, oxazoline, thiazoline, pyrrole, oxazole, thiazole, selenazole, imidazole, tetrazole and pyridine nuclei; nuclei formed by coalescence of alicyclic hydrocarbon rings to these nuclei; and nuclei formed by fusion of aromatic hydrocarbon rings to the above-illustrated nuclei, such as indolenine, benzindolenine, indole, benzoxazole, naphthooxazole, benzothiazole, naphthothiazole, benzoselenazole, benzimidazole and quinoline nuclei. These nuclei may be substituted on carbon atoms.

The following 5- to 6-membered heterocyclic nuclei structure for merocyanine dye or compound merocyanine dye: pyrazoline-5-one nucleus, thiohydantoin nucleus, 2-thiooxazolidine-2,4-dione nucleus, thiazolidine-2,4-dione nucleus, Rhodamine nucleus and thiobarbituric acid nucleus.

These sensitizing dyes may be used either singly or in combination. In particular, combinations of these sensitizing dyes are frequently used for super sensitization.

Aside from the above-identified sensitizing dyes, it is also possible to incorporate in the emulsion dyes which have no spectral sensitization effects or substances which are substantially incapable of absorbing visible rays and which show the super sensitization ability. Exemplary substances which may be thus incorporated include aminostyr compounds substituted with nitrogen-containing heterocyclic groups (e.g., those compounds described in U.S. Pat. Nos. 2,933,390 and 3,635,721), aromatic organic acid formaldehyde condensation products (e.g., those compounds described in U.S. Pat. No. 3,743,510), cadmium salts and azaindene compounds.

The present invention may be applied for multilayer multi-color photographic materials having at least two different degrees of spectral sensitivity on the substrate. Multilayer natural color photographic materials usually have on the substrate at least one each of red-sensitive, green-sensitive and blue-sensitive emulsion layers. The order of these layers may be selected optionally as required. Generally a cyanogen-forming, magenta-forming and yellow-forming couplers are incorporated into the red-sensitive, green-sensitive and blue-sensitive emulsion layers, respectively, but different combinations are possible in some cases.

In this photographic emulsion layer of the sensitive material made in accordance with the present invention or other photographic emulsion layers or non-sensitive layers, together with the above-illustrated compounds of the present invention, other dye-forming couplers, i.e., compounds which may develop colors by oxidative coupling with aromatic primary amine developing agents (e.g., phenylenediamine derivatives and aminophenol derivatives) in the color developing process. Exemplary Magenta couplers include 5-pyrazolone coupler, pyrazolobenzimidazole coupler, pyrazoloimidazol coupler, pyrazolopyrazole coupler, pyrazolotriazole coupler, pyrazolotetrazole coupler, cyanoacetylcoumarone coupler and open chain acylacetonitrile coupler. Exemplary yellow couplers include acylacetamide couplers (e.g., benzoylacetanilides and pivaloylacetanilides). Exemplary cyanogen couplers include naphthol coupler and phenol coupler. These couplers are desirably of a non diffusive type and contain a hydrophobic group called a ballast group in the molecule. The couplers may also be in the form of polymers. The couplers may be either four- or two-equivalent with respect to silver ion. The couplers may also be colored couplers having color correction effects or couplers which release development restrainers in the course of development (i.e., the so-called DIR couplers).

In addition to the DIR couplers, colorless DIR coupling compounds which produce colorless substances by a coupling reaction and which release development restrainers may also be incorporated in the above-identified layers. Aside from DIR couplers, compounds which release development restrainers in the course of development may be incorporated in the sensitive material.

In order to meet the requirements for a sensitive material, two or more different kinds of the above-illustrated couplers may be used in the same layer of the photographic material of the present invention. Needless to say, the same compound may be added to two or more different layers of the photographic material of the present invention.

Inorganic or organic hardners may be incorporated in the hydrophilic colloid layers such as the photographic emulsion layer. For example, the following substances may be used either singly or in combination:

Chromium salts (e.g., chromium alum and chromium acetate), aldehydes (e.g., formaldehyde, glyoxal and glutaraldehyde), N-methylol compounds (e.g., dimethylol urea and methylol dimethylhydantoin), dioxane derivatives (e.g., 2,3-dihydroxydioxane), active vinyl compounds (e.g., 1,3,5-triacryloyl-hexahydro-s-triazine and 1,3-vinylsulfonyl-2-propanol), active halides (e.g., 2,4-dichlor-6-hydroxy-s-triazine) and mucohalogenic acids (e.g., mucochloric acid and mucophenoxychloric acid).

If dyes or ultraviolet ray absorbing agents are incorporated in the hydrophilic colloid layers of the photographic material made in accordance with the present invention, the dyes or the UV ray absorbing agents may be mordanted with cationic polymers and the like.

The sensitive material made in accordance with the present invention may contain as an anti-color-fogging agent derivatives of hydroquinone, aminophenol, gallic acid and ascorbic acid.

The photographic material made in accordance with the present invention may contain an ultraviolet ray absorbing agent in the hydrophilic colloid layer. Exemplary compounds to be used include benzotriazole compounds substituted with an aryl group (e.g., those described in U.S. Pat. No. 3,533,794), 4-thiazolidone compounds (e.g., those described in U.S. Pat. Nos. 3,314,794 and 3,352,681), benzophenone compounds (e.g., those described in Japanese Patent Application (OPI) No. 2,784/71), cinnamic acid ester compounds (e.g., those described in U.S. Pat. Nos. 3,705,805 and 3,707,375), butadiene compounds (e.g., those described in U.S. Pat. No. 4,045,229) an benzooxidol compounds (e.g , those described in U.S. Pat. No. 3,700,455). An ultraviolet ray absorbing coupler (e.g., cyanogen dye forming coupler of α-naphthol) or an ultraviolet ray absorbing polymer may also be used. These ultraviolet ray absorbing agents may be mordanted in specific layers.

The sensitive material made in accordance with the present invention may contain a water-soluble dye as a filter dye or for various purposes such as prevention of irradiation in the hydrophilic colloid layer Exemplary dyes to be used include oxonol, hemioxonol, styryl, merocyanine, cyanine and azo dyes Among these, oxonol dyes, hemioxonol dyes and merocyanine dyes are particularly useful.

In accordance with the present invention, the following known anti-fading agents may be incorporated in the photographic material, and the color image stabilizers used in the present invention may be employed either singly or in combination. Known anti-fading agents include hydroquinone derivatives, gallic acid derivatives, p-alkoxyphenols, p-oxyphenol derivatives and bisphenols.

In the photographic processing of the silver halide photographic material of the present invention, any suitable known method can be employed, utilizing any known processing solution. The processing temperature is usually chosen within the range of 18° C. to 50° C., but temperatures lower than 18° C. or higher than 50° C. may also be employed. Either of the monochrome development process wherein a silver image is formed in accordance with specific purposes and the color photographic development process wherein dye images are formed may be applied for the silver halide photographic material of the present invention.

The developer solution used in monochrome development may contain a conventionally known developing agent. Exemplary developing agents which may be employed either singly or in combination include:

Dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and heterocyclic compounds produced by condensation of 1,2,3,4-tetrahydroquinoline rings and indolene rings, such as those described in U.S. Pat. No. 4,067,872. In addition to these compounds, the developer solution generally contains a known preservative, alkaline agent, pH buffer, anti-fogging agent and the like, and may contain, as required, a solubilizer, color toning agent, development accelerator, surfactant, antifoaming agent, water softener, hardener, tackifier and the like.

As the fixing solution, the commonly used composition may be employed. Exemplary fixing agents include thiosulfate, thiocyanate, and an organic sulfur compounds which are known to have fixing effects. The fixing solution may contain a water-soluble aluminum salt as the hardener.

Conventional methods may be employed for forming dye images. Exemplary methods include 1) the negative-positive process (see "Journal of the Society of Motion Picture and Television Engineers, vol. 61, pp. 667-701, 1973), 2) the color reversal process comprising forming negative silver images by developing a film in a developer solution containing a black and white developing agent and performing a suitable anti-fogging treatment such as at least one cycle of uniform exposure, followed by color development to form positive dye images, and 3) the silver dye bleach process comprising subjecting the photographic emulsion layer containing dyes to exposure followed by development to form silver images and then bleaching the dyes using the silver images as the bleaching catalyst The color developer solution generally consists of an aqueous alkaline solution containing a color developing agent. Exemplary color developing agents to be used in the present invention include known primary aromatic amine developing agents such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline, 4-amino-3-methyl-N-ethyl-N-β-methoxyethylaniline and the like).

In addition to the above-illustrated developing agents, those compounds described on pp. 226-229 of "Photographic Processing Chemistry" by L. F. A. Mason (published by Focal Press, 1966), U.S. Pat. Nos. 2,193,015 and 2,592,364 and Japanese Patent Application (OPI) No. 64,933/73, may also be employed The color developer solution may, in addition to the above-listed compounds, contain a pH buffer such as sulfite, carbonate, borate and phosphate of alkali metals, a development restrainer or anti-fogging agent such as bromide, iodide and an organic anti-fogging agent. The development solution may also, as required, contain a water softener, preservative such as hydroxylamine, organic solvent such as benzyl alcohol and diethylene glycol, development accelerator such as polyethylene glycol, quaternary ammonium salts and amines, dye forming coupler, competitive coupler, a fogging agent such as sodium borohydride, an auxiliary developing agent such as 1-phenyl-3-pyrazolidone, a tackifier, polycarboxylic acid compounds used as chelate agents as described in U.S. Pat. No. 4,083,723, and an anti-oxidizing agent as described in West German Offenlegungsschrift (OLS) No. 2,622,950.

The photographic emulsion layer is usually subjected to bleaching after completion of the color development process. The bleach process may or may not be performed simultaneously with the fixation process. Exemplary bleaching agents include compounds of polyvalent metals such as iron (II), cobalt (III), chromium (VI) and copper (II), peracids, quinones and nitroso compounds. Specifically, ferricyanide, dichromate, organic complex salts of iron (III) or cobalt (III), complex salts of aminopolycarboxylic acids such as ethylenediamine tetraacetic acid, nitrilotriacetic acid and 1,3-diamino-2-propanol tetraacetic acid, or of organic acids such as citric acid, tartaric acid and malic acid; persulfate and permanganate; and nitrosophenol. Among these particularly useful are potassium ferricyanide EDTA iron (III) sodium and EDTA iron (III) ammonium. Complex salts of EDTA iron (III) are useful both in an independent bleaching solution and a combined bleaching and fixing solution.

Various additives may be added to the bleaching or bleaching and fixing solution, in addition to the bleaching accelerators as described in U.S. Pat. Nos. 3,042,520 and 3,241,966, and Japanese Patent Application Publication Nos. 8,506/70 and 8,836/70, and the thiol compounds as described in Japanese Patent Application (OPI) No. 65,732/78.

The photographic DIR compound of the present invention may be used for various silver halide photographic materials. It is useful for both the black and white photography and the color photography. The compound of the present invention may also be employed for various silver halide photographic materials used for the general black and white photography, monochrome printing, X-ray, micro lithography with electron beams, high resolution black and white photography, diffusion transfer black and white photography, general color photography, color X-ray, diffusion transfer color photography and the like.

The DIR compound of the present invention is highly active and quickly releases a development restrainer by oxidation. Because of this advantage, addition of only a small amount of this compound produces DIR effects such as the tone control, finer-grain images, increased sharpness, better color reproduction and the like. Further, the DIR compound of the present invention is stable in the silver halide photographic material and does not cause deterioration of shelf stability of the photographic material.

The DIR compound of the present invention is free from any accumulation of a development restrainer in the developer solution which may adversely affect the development process when the photographic material is processed in large quantities. Thus, the desired DIR effects may be obtained.

The present invention will now be further described in detail by reference to the following Examples, which should not be construed to limit the scope of the invention in any manner.

EXAMPLE 1

A multilayer color photographic material comprising layers of the following compositions was prepared on a cellulose triacetate film substrate.

| | |
|---|---|
| First layer: | antihalation layer (AHL) a gelatin layer containing black colloidal silver |
| Second layer: | middle layer a gelatin layer containing an emulsified dispersion of 2,5-di-t-octylhydroquinone |
| Third layer: | first red sensitive emulsion layer ($RL_1$) Silver iodobromide emulsion (silver iodobromide: 5 mol %): amount of silver coated: 1.79 g/m$^2$ Sensitizing dye I: $6 \times 10^{-5}$ mol per mol of silver Sensitizing dye II: $1.5 \times 10^{-5}$ mol per mol of silver Coupler A: 0.04 mol per mol of silver Coupler C-1: 0.0015 mol per mol of silver Coupler C-2: 0.0015 mol per mol of silver Above-identified Compound No. 3: 0.0006 mol per mol of silver |
| Fourth layer: | second red sensitive emulsion layer ($RL_2$) Silver iodobromide emulsion (silver iodide; 4 mol %): amount of silver coated: 1.4 g/m$^2$ Sensitizing dye I: $3 \times 10^{-5}$ mol per mol of silver Sensitizing dye II: $1.2 \times 10^{-5}$ mol per mol of silver Coupler A: 0.005 mol per mol of silver Coupler C-1: 0.0008 mol per mol of silver Coupler C-2: 0.0008 mol per mol of silver Above-identified Compound No. 3: 0.00006 mol per mol of silver |
| Fifth layer: | middle layer (ML) Same as the second layer |
| Sixth layer: | first green sensitive emulsion layer ($GL_1$) Silver iodobromide emulsion (silver iodide: 4 mol %): amount of silver coated: 1.5 g/m$^2$ Sensitizing dye III: $3 \times 10^{-5}$ mol per mol of silver Sensitizing dye IV: $1 \times 10^{-5}$ mol per mol of silver Coupler B: 0.05 mol per mol of silver Coupler M-1: 0.008 mol per mol of silver Above-identified Compound No. 3: 0.0015 mol per mol of silver |
| Seventh layer: | second green sensitive emulsion layer ($GL_2$) Silver iodobromide emulsion (silver iodide: 5 mol %): amount of silver coated: 1.6 g/m$^2$ Sensitizing dye III: $2.5 \times 10^{-5}$ mol per mol of silver Sensitizing dye IV: $0.8 \times 10^{-5}$ mol per mol of silver Coupler B: 0.02 mol per mol of silver Coupler M-1: 0.003 mol per mol of silver Above-identified Compound No. 3: 0.0003 mol per mol of silver |
| Eighth layer: | yellow filter layer (YEL) A gelatin layer containing in the aqueous gelatin solution an emulsified dispersion of yellow colloidal silver and 2,5-di-t-octylhydroquinone |
| Ninth layer: | first blue sensitive emulsion layer ($BL_1$) Silver iodobromide emulsion (silver iodide: 6 mol %): amount of silver coated: 1.5 g/m$^2$ Coupler Y-1: 0.25 mol per mol of silver |
| Tenth layer: | second blue sensitive emulsion layer ($BL_2$) Silver iodobromide (silver iodine: 6 mol %) amount of silver coated: 1.1 g/m$^2$ Coupler Y-1: 0.06 mol per mol of silver |
| Eleventh layer: | protective layer (PL) Coating of a gelatin layer containing polymethyl methacrylate particles (diameter: about 1.5 μ). |

In addition to the above-identified ingredients, a gelatin hardener and a surfactant were added to the layers.

The sample prepared as above was named Sample No. 101.

Sample No. 102: This sample was prepared in the same manner as Sample No. 101 except that 1) Compound No. 3 added to $RL_1$ and $RL_2$ was replaced by an equal amount of Compound No. 7, and 2) Compound No. 3 added to $GL_1$ and $GL_2$ was replaced by Compound No. 14 which was used in an amount twice that of Compound No. 3.

Sample No. 103: This sample was prepared in the same manner as Sample No. 101 except that Compound No. 3 of Sample No. 101 was replaced by an equal amount of a DIR compound (DIR-1).

Sample No. 104: This sample was prepared in the same manner as Sample No. 101 except that Compound No. 3 of Sample No. 101 was replaced by an equal amount of a DIR compound (DIR-2).

Sample No. 105: This sample was prepared in the same manner as Sample No. 101 except that Compound No.3 of Sample No. 101 was replaced by an equimolar amount of Compound No. 58.

Sample No. 106: This sample was prepared in the same manner as Sample No. 101 except that Compound No.3 of Sample No.101 was replaced by an equimolar amount of Compound No. 72.

DIR compounds used as control

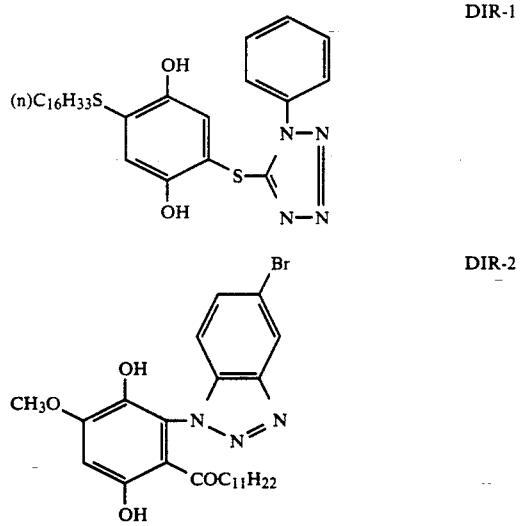

COMPOUNDS USED FOR PREPARATION OF THE SAMPLES

Sensitizing dye I: pyridinium salt of anhydro-5,5'-dichloro-3,3'-di-(γ-sulfopropyl) -9-ethyl-thiacarbocyaninehydroxide.

Sensitizing dye II: triethylamine salt of anhydro-9-ethyl-3,3'-di-(γ-sulfopropyl) -4,5,4',5'-dibenzothiacarbocyaninehydroxide.

Sensitizing dye III: sodium salt of anhydro-9-ethyl-5,5'-dichloro-3,3'-di-(γ-sulfopropyl)oxacarbocyanine.

Sensitizing dye IV: sodium salt of anhydro-5,6,5',6'-tetrachloro-1,1'-diethyl-3,3'-di-β-[β-(γ-sulfopropoxy)ethoxy]ethylimidazolocarbocyaninehydroxide.

Coupler A
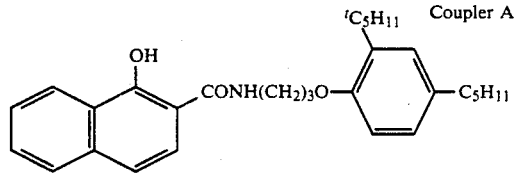

Coupler B
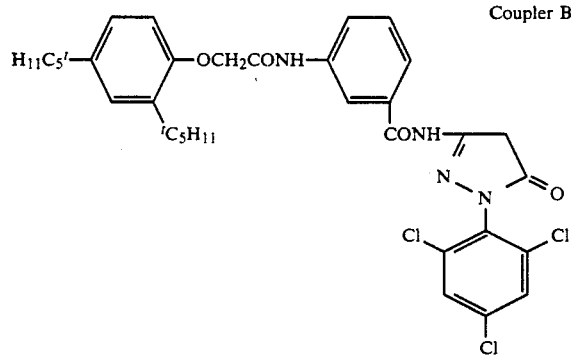

Coupler C-1
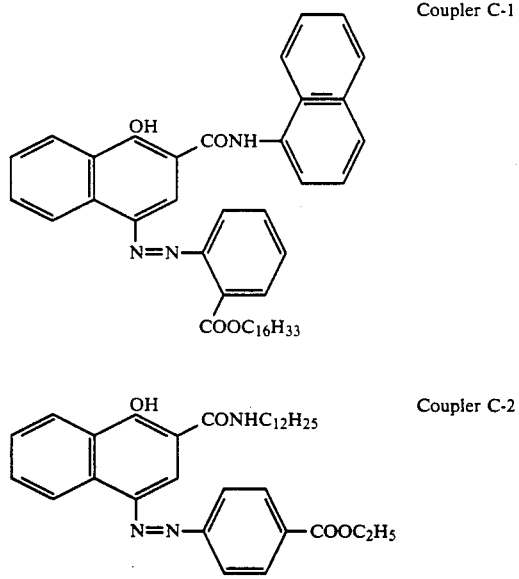

Coupler C-2

Coupler M-1
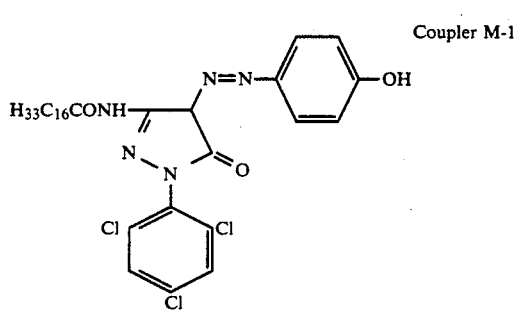

-continued

Coupler Y-1
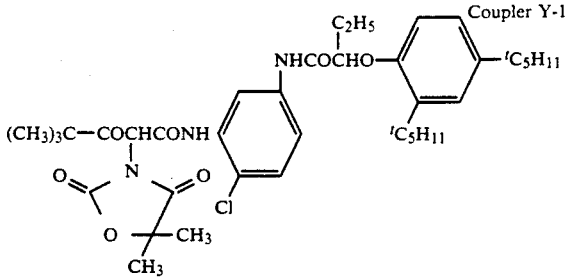

The obtained Samples Nos. 101 to 104 were made into 35 mm size films, followed by wedge exposure. A 600 m portion of each of these films was subjected to the following development process in a 2-liter developer solution tank.

| | |
|---|---|
| 1. Color development | 3 min 15 sec |
| 2. Bleach | 6 min 30 sec |
| 3. Rinsing | 3 min 15 sec |
| 4. Fixation | 6 min 30 sec |
| 5. Rinsing | 3 min 15 sec |
| 6. Stabilization | 3 min 15 sec |

The compositions of the processing solutions used for the above steps are shown below:

| | |
|---|---|
| Color developer solution | |
| Sodium nitrilotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N-ethyl-N-8-hydroxyethylamino)-2-methyl-aniline sulfate | 4.5 g |
| Water to make | 1 liter |
| Bleaching solution | |
| Ammonium bromide | 160.0 g |
| Aqueous ammonia (28%) | 25.0 ml |
| EDTA sodium iron salt | 130 g |
| Glacial acetic acid | 14 ml |
| Water to make | 1 liter |
| Fixing solution | |
| Sodium tetrapolyphosphate | 2.0 g |
| Sodium sulfite | 4.0 g |
| Ammonium thiosulfate (70%) | 175.0 ml |
| Sodium bisulfite | 4.6 g |
| Water to make | 1 liter |
| Stabilizing solution | |
| Formalin | 8.0 ml |
| Water to make | 1 liter |

The overflow portion of the developing solution was subjected to the following recycle treatment for repeated reuse.

The recycle treatment was performed batch-wise. The overflow solution was introduced into an electric dialyzer and electric dialysis was performed until the amount of KBr became not greater than 0.7 g/l.

To this solution were added sodium nitrilotriacetate, sodium sulfite, sodium carbonate, potassium bromide, hydroxylamine sulfate and 4-(N-ethyl-N-β-hydroxyethylamino)-2-methyl-aniline sulfate, which were all consumed in the running. The mixture was subjected to pH adjustment to a final pH of 10.05 and the resultant solution was reused as a replenisher. Table 1 shows the decrease in sensitivity after 10 cycles of reuse (1 liter of the overflow solution was used for 1 reuse cycle).

As is clear from the results shown in Table 1, Samples Nos. 101, 102, 105 and 106 showed no substantial sensitivity decrease, whereas Samples Nos. 103 and 104 suffered a large drop in sensitivity. This result shows that the groups which left Compounds Nos. 3, 7, 14, 58 and 72 form, in the color developing solution, compounds which have no photographic effects, and are not accumulated in the developer solution, as in the case of other non-deactivating type leaving groups, making repeated reuse of the solution possible.

TABLE 1

| Sample No. | ΔSfog* + 0.3 | | |
|---|---|---|---|
| | B | G | R |
| 101 | +0.02 | ±0 | ±0 |
| 102 | +0.03 | −0.02 | ±0 |
| 103 | −0.21 | −0.13 | −0.06 |
| 104 | −0.16 | −0.07 | ±0 |
| 105 | +0.02 | ±0 | ±0 |
| 106 | +0.04 | −0.01 | ±0 |

*The sensitivity drop at (fog + 0.3) density is expressed by log E.

EXAMPLE 2

Sample No. 201: This sample was prepared in the same manner as Sample No. 101 except that compound No. 3 for Sample No. 101 was replaced by Compound No. 5 which was used in an amount 1.2 times as much as that of Sample No. 3.

Sample No. 202: This sample was prepared in the same manner as Sample No. 101 except that compound No. 3 of Sample No. 101 was replaced by Compound No. 15 which was used in an amount twice that of Sample No. 3.

Sample No. 203: This sample was prepared in the same manner as Sample No. 101 except that Compound No. 3 of Sample No. 101 was replaced by an equal amount of a DIR compound (DIR-3).

DIR compound (DIR-3) used as control

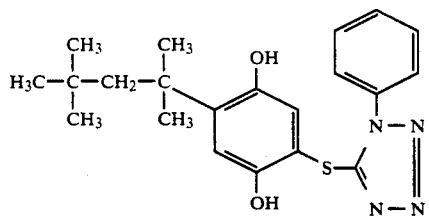

Each of Samples Nos. 201 to 203 was made into a 35 mm film, and this film was subjected to wedge exposure. Then a 100 m portion of each of the films was subjected to the same development procedure as that of Example No. 1 in a tank containing 5 liters of the developing solution. The sensitivity of the first portion of each of the processed samples was compared with that of the end portion, and the decrease in sensitivity of the end portion of each of the samples is shown in Table 2.

As is clear from the results shown in Table 2, Samples Nos. 201 and 202 suffers from a smaller sensitivity drop than Sample No. 203. This means that the groups which left Compounds Nos. 5 and 15 were converted in the color developing solution into compounds which have no substantial photographic effects.

TABLE 2

| Sample No. | ΔSfog* + 0.3 | | |
|---|---|---|---|
| | B | G | R |
| 201 | +0.01 | ±0 | ±0 |
| 202 | +0.03 | +0.01 | ±0 |
| 203 | −0.22 | −0.14 | −0.07 |

*The sensitivity drop at (fog + 0.3) density is expressed by log E.

EXAMPLE 3

A silver halide emulsion comprising 80 mol % silver chloride, 19.5 mol % silver bromide and 0.5 mol % silver iodide was prepared by gold sensitization and sulfur sensitization according to the conventional method. The gelatin contained in this emulsion was 45% based on the weight of the silver halide. To this emulsion were added potassium salt of 5-[3-(6 sulfobutyl)-5-chloro-2-oxazolidilideneethylidene]-1-hydroxyethoxyethyl-3-(2-pyridyl)-2-thiohydantoin (spectral sensitizer), sodium dodecylbenzenesulfonate (surfactant) and the polymer later described in Formulation No. 3 of a preparation example of U.S. Pat. No. 3,525,620. Then, 1,2-bis(vinylsulfonylacetamido)ethane (hardener) was added to the resulting mixture to a final ratio of 2.6% based on the total dry weight of the gelatin used in the composition (i.e., the total dry gelatin including that which was added to the non-photosensitive upper layer which will be described below). Finally, the compound of the present invention was added to the resulting mixture in the form of a methanol solution as shown in Table 3 to obtain a coating solution for a photographic silver halide emulsion layer.

On the other hand, a coating solution for the non-sensitive upper layer was prepared separately by adding to a 5% gelatin solution sodium dodecylbenzenesulfonate (surfactant) and a polymethylmethacrylate latex (matting agent) having an average grain size of 3.0 to 4.0μ.

Then, the above-identified coating solution for the silver halide emulsion layer and the coating solution for the non-sensitive upper layer were applied to a polyethylene terephthalate substrate by the two-coat simultaneous coating method. The amount of silver coated was 3.0 g/m², and the thickness of the dried film of the non-sensitive upper layer was 1.0μ.

These samples were exposed to white tungsten light for 8 seconds through an optical step wedge having a density difference of 0.1 between two adjacent steps.

Then, half-tone images were formed on these samples by the following method:

A commercial negative grey contact screen (150 lines/inch) was brought into close contact with the samples and the samples were exposed to white tungsten light for 10 seconds through an optical step wedge having a density difference of 0.1.

The above-identified exposed samples were developed in the following developing solution at 38° C. for 20 seconds, followed by fixation, rinsing and drying by the conventional method.

| Composition of the developer solution | |
|---|---|
| Sodium sulfite | 75 g |
| Sodium hydrogencarbonate | 7 g |
| Hydroquinone | 40 g |
| 1-phenyl-4,4-dimethyl-3-pyrazolidone | 0.4 g |
| Sodium bromide | 3 g |
| 5-methylbenzotriazole | 0.8 g |
| Ethylenediamine tetraacetic acid sodium salt | 1 g |

-continued

| Composition of the developer solution | |
|---|---|
| 3-diethylamino-1,2-propanediol | 20 g |
| Water to make | 1 liter |
| Adjustment to pH = 11.4 | |

The relative sensitivity and the results of γ evaluation are shown in Table 3.

TABLE 3

| Sample No. | Compound | Amount added | Relative sensitivity* | γ |
|---|---|---|---|---|
| 301 | — | — | 100 | 5.2 |
| 302 | (7) | $3.0 \times 10^{-4}$ mol/mol Ag | 90 | 3.5 |
| 303 | (34) | $3.0 \times 10^{-4}$ mol/mol Ag | 90 | 3.4 |
| 304 | (36) | $3.0 \times 10^{-4}$ mol/mol Ag | 90 | 3.4 |
| 305 | (45) | $3.0 \times 10^{-4}$ mol/mol Ag | 85 | 3.1 |
| 306 | (46) | $3.0 \times 10^{-4}$ mol/mol Ag | 90 | 3.4 |

*The relative sensitivity was determined with a density of 1.5 taken as 100.

As is clear from Table 3, the compound of the present invention provides the desired DIR effects and particularly the tone softening effect.

EXAMPLE 4

Sample No. 307 was prepared in the same manner as Sample No. 302 except that compound No. 7 for Sample No. 302 of Example 3 was replaced by an equal amount of a DIR compound (DIR-1), and this Sample No. 307 was used for comparison purposes.

Each of Samples Nos. 301 to 307 was made into 3×15 cm sample film portions. One thousand sample portions of each of Samples Nos. 301 to 307 were subjected to the same developing procedure of Example 3, and the sensitivity of the first portion of each of the processed samples was compared with that of the end portion. The results are shown in Table 4.

TABLE 4

| Sample No. | Compound | Relative sensitivity* |
|---|---|---|
| 301 | — | 100 |
| 302 | (7) | 97 |
| 303 | (34) | 95 |
| 304 | (35) | 98 |
| 305 | (42) | 95 |
| 306 | (44) | 95 |
| 307 | DIR-1 | 75 |

*Relative sensitivity was compared at a density of 0.2

As is clear from these results, Samples Nos. 302 to 306 containing the compounds of the present invention suffer from smaller sensitivity drops than Sample No. 307. This means that the compounds of the present invention, after being dissolved in the developer solution, are converted into compounds which have no substantial effects on the photographic processing.

While the invention has been described in detail and with reference to specific embodiments thereof, it will be apparent to one skilled in the art that various changes and modifications can be made therein without departing from the spirit and scope thereof.

What is claimed is:

1. A silver halide photographic material containing at least one silver halide emulsion layer wherein said at least one silver halide emulsion layer or a photographic auxiliary layer contains at least one development restrainer-releasing redox compound which is represented by the formula (I):

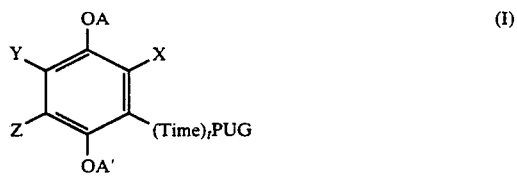

wherein X, Y and Z are each an electron withdrawing group, a hydrogen atom, a halogen atom, a substituted or unsubstituted alkyl group having 1 to 20 carbon atoms, a substituted or unsubstituted alkoxy group having 1 to 20 carbon atoms, a substituted or unsubstituted aryl group having 6 to 20 carbon toms, or an alkylthio group having 1 to 20 carbon atoms; Time is a timing group; t is 0 or 1; PUG is a development restrainer which, after being released by a reaction with a light-exposed silver halide and/or an oxidized product of the developing agent, becomes converted in a developing solution into a compound having substantially no development restraining ability or showing a marked decrease in development restraining ability; Time-PUG or PUG is bonded to the benzene nucleus via a sulfur atom, a nitrogen atom or a selenium atom; and A and A' each represents hydrogen or a group which is hydrolyzable by an alkali.

2. A silver halide photographic material as claimed in claim 1, wherein said compound is employed in an amount of from $10^{-6}$ to 1 mol per mol of silver.

3. A silver halide photographic material as claimed in claim 1, wherein said compound is employed in an amount of from $10^{-5}$ to $10^{-1}$ mol per mol of silver.

4. A silver halide photographic material as claimed in claim 1, wherein said PUG is represented by formula (II):

—AF—CCD    (II)

wherein AF—CCD is selected from the group consisting of:

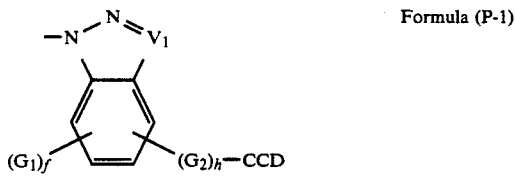

Formula (P-1)

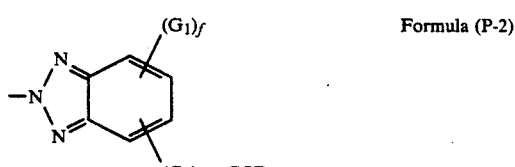

Formula (P-2)

Formula (P-3)

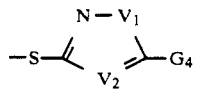
Formula (P-4)

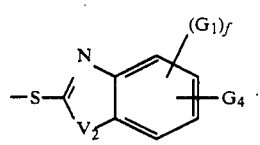
Formula (P-5)

wherein $G_1$ is a hydrogen atom, a halogen atom, an alkyl group having 1 to 20 carbon atoms, an acylamino group, an alkoxy group, a sulfonamido group, an alkylthio group, an alkylamino group, an anilino group, an amino group, an alkoxycarbonyl group, an acyloxy group, a nitro group, a cyano group, a sulfonyl group, an aryloxy group, a hydroxyl group, a thioamido group, a carbamoyl group, a sulfamoyl group, a carboxyl group, a ureido group, or an aryloxycarbonyl group; $G_2$ is any one of those groups listed for $G_1$, which can form a divalent group; $G_3$ is a substituted or unsubstituted alkylene group or a substituted or unsubstituted arylene group; $V_1$ is a nitrogen atom or a methine group; $V_2$ is an oxygen atom, a sulfur atom,

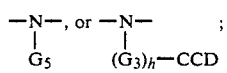

$G_4$ is any one of those groups listed for $G_1$ or $(G_3)_h$—CCD; $G_5$ is a hydrogen atom, an alkyl group having 1 to 20 carbon atoms, or an aryl group having 6 to 20 carbon atoms; f is an integer of 1 or 2; and h is 0 or 1, where in the formulae (P-4) and (P-5), at least one of the groups represented by $V_2$ and $G_4$ contains CCD, wherein the group represented by CCD is represented by one of the following formulae (D-1) to (D-16);

—COOR$^8$       Formula (D-1)

Formula (D-2)

wherein $R^8$ and $R^9$ are each a substituted or unsubstituted alkyl group having 1 to 20 carbon atoms, a substituted or unsubstituted aryl group having 6 to 20 carbon atoms or a substituted or unsubstituted aralkyl group;

Formula (D-3)

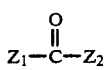
Formula (D-4)

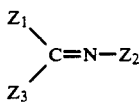
Formula (D-5)

wherein $Z_1$ and $Z_2$ are each a bond to AF or a hydrogen atom, an alkylamino group, an alkyl group having 1 to 20 carbon atoms, an aryl group having 6 to 20 carbon atoms, an acylamino group, or a 4- or 7-membered substituted or unsubstituted heterocyclic group containing, as the hetero atom, a nitrogen atom, a sulfur atom, or an oxygen atom; $Z_3$ is a hydrogen atom, a halogen atom, an alkyl group having 1 to 20 carbon atoms, an aryl group having 6 to 20 carbon toms, a heterocyclic group, an alkoxy group, an acyl group, a carbamoyl group, a sulfamoyl group, a sulfonyl group, an alkoxycarbonyl group, an acylamino group, a sulfonamido group, an alkylthio group, or a ureido group; or $Z_1$ and $Z_3$ are taken together to form a ring; $Z_4$ is a group of atoms selected from the group consisting of a carbon atom, a nitrogen atom, an oxygen atom, and a sulfur atom, which can form a 5- or 6-membered unsaturated heterocyclic ring; and $X^e$ is an organic sulfonic acid anion, an organic carboxylic acid anion, a halogen ion, or an inorganic anion;

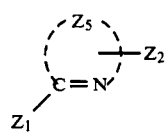
Formula (D-6)

wherein $Z_1$ and $Z_2$ are as defined above; and $Z_5$ is a group of atoms selected from the group consisting of a carbon atom, an oxygen atom, and a nitrogen atom, which, together with

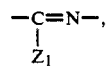

can form a 5- to 7-membered ring and which does not give aromatic group properties to

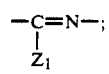

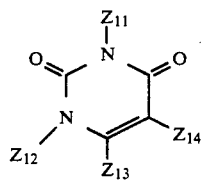
Formula (D-7)

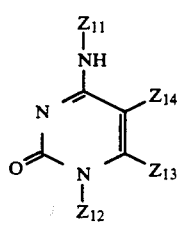
Formula (D-8)

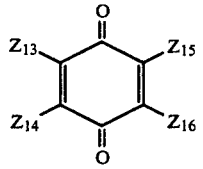
Formula (D-9)

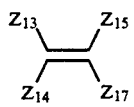
Formula (D-10)

wherein at least one of $Z_{11}$ to $Z_{17}$ is one of those groups defined for AF or a group containing an AF group; $Z_{11}$ and $Z_{12}$ are each a hydrogen atom, an alkyl group having 1 to 20 carbon atoms, an aryl group having 6 to 20 carbon atoms, or an AF group; $Z_{13}$, $Z_{14}$, $Z_{15}$, and $Z_{16}$ are each a hydrogen atom, an alkyl group having 1 to 12 carbon atoms, an aryl group having 6 to 20 carbon atoms, a halogen atom, an aryloxy group, an arylthio group, an alkylthio group, an alkoxycarbonyl group, an aryloxycarbonyl group, an alkanesulfonyl group, a sulfamoyl group, a carbamoyl group, a ureido group, an acyl group, an acylamino group, an arylsulfonyl group, a heterocyclic group, an acyloxy group, a nitro group, a cyano group, a carboxyl group, a thiocarbamoyl group, a sulfamoylamino group a diacylamino group, or an AF group; $Z_{17}$ is a halogen atom, an alkoxycarbonyl group, an aryloxycarbonyl group, an alkanesulfonyl group, a sulfamoyl group, a carbamoyl group, an acyl group, a diacylamino group, an arylsulfonyl group, a heterocyclic group, a nitro group, a cyano group, a carboxyl group, or a sulfonamido group, provided that AF can be bonded through one of the foregoing groups which can form a divalent group; in formula (D-9), $Z_{15}$ and $Z_{16}$ can each form a divalent group and, when taken together, can form a ring; and in formula (D-10), $Z_{15}$ and $Z_{17}$ can each form a divalent group and, when taken together, can form a ring;

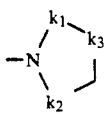

Formula (D-11)

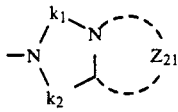

Formula (D-12)

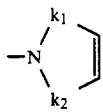

Formula (D-13)

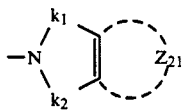

Formula (D-14)

wherein $Z_{21}$ is a saturated or unsaturated 6-membered ring; $k_1$ and $k_2$ are each an electron attractive group; $k_3$ is —N—R wherein R is an alkyl group having not more than 6 carbon atoms;

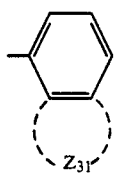

Formula (D-15)

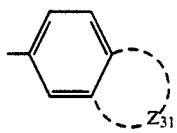

Formula (D-16)

wherein $Z_{31}$ is a group which can form a 5- or 6-membered lactone ring or a 5-membered cyclic imide.

5. A silver halide photographic material as claimed in claim 4, wherein said CCD is represented by formula (D-1).

6. A silver halide photographic material containing at least one silver halide emulsion layer wherein said at least one silver halide emulsion layer or a photographic auxiliary layer contains at least one development restrainer-releasing redox compound which is represented by the formula (III):

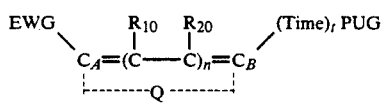

wherein EWG is an electron withdrawing group having a Hammett's $\sigma$ para value exceeding 0.3; Q is an atomic group which bonds to $C_A$ and $C_B$ and forms a substituted benzene ring-type oxidation-reduction moiety from which time—PUG is released first by oxidation during photographic development processing; $C_A$ and $C_B$ are each a carbon atom which conjugates EWG with Time—PUG via a substituted ethylene bond or its vinylog, when the development restrainer-releasing redox compounds is oxidized; $R_{10}$ and $R_{20}$ are each a hydrogen atom or a substituent; Time is a timing group; t is 0 or 1; PUG is a development restrainer which, after being released by a reaction with a light-exposed silver halide and/or an oxidized product of the developing agent, becomes converted in a developing solution into a compound having substantially no development restraining ability or showing a marked decrease in development restraining ability; Time—PUG or PUG is connected with $C_B$ via a sulfur atom, a nitrogen or a selenium atom; and n is an integer of 0 or 1.

7. A silver halide photographic material as claimed in claim 6, wherein said compound is employed in an amount of from $10^{-6}$ to 1 mol per mol of silver.

8. A silver halide photographic material as claimed in claim 7, wherein said compound is employed in an amount of from $10^{-5}$ to $10^{-1}$ mol per mol of silver.

9. A silver halide photographic material as claimed in claim 6, wherein said PUG is represented by formula (II):

wherein AF—CCD is selected from the group consisting of:

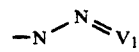

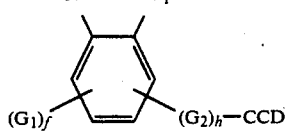

Formula (P-1)

-continued

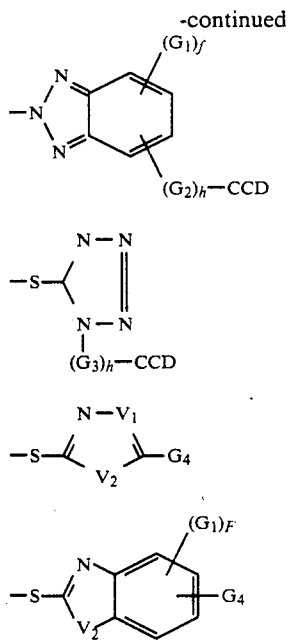

wherein $G_1$ is a hydrogen atom, a halogen atom, an alkyl group having 1 to 20 carbon atoms, an acylamino group, an alkoxy group, a sulfonamido group, an alkylthio group, an alkylamino group, an anilino group, an amino group, an alkoxycarbonyl group, an acyloxy group, a nitro group, a cyano group, a sulfonyl group, an aryloxy group, a hydroxyl group, a thioamido group, a carbamoyl group, a sulfamoyl group, a carboxyl group, a ureido group, or an aryloxycarbonyl group; $G_2$ is any one of those groups listed for $G_1$, which can form a divalent group; $G_3$ is a substituted or unsubstituted alkylene group or a substituted or unsubstituted arylene group; $V_1$ is a nitrogen atom or a methine group; $V_2$ is an oxygen atom, a sulfur atom,

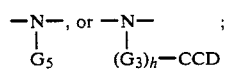

$G_4$ is any one of those groups listed for $G_1$ or $(G_3)_h$—CCD; $G_5$ is a hydrogen atom; an alkyl group having 1 to 20 carbon atoms, or an aryl group having 6 to 20 carbon atoms; f is an integer of 1 or 2; and h is 0 or 1; where in the formulae (P-4) and (P-5), at least one of the groups represented by $V_2$ and $G_4$ contains CCD, wherein the group represented by CCD is represented by one of the following formulae (D-1) to (D-16):

—COOR$^8$      Formula (D-1)

      Formula (D-2)

wherein $R^8$ and $R^9$ are each a substituted or unsubstituted alkyl group having 1 to 20 carbon atoms, a substituted or unsubstituted aryl group having 6 to 20 carbon atoms or a substituted or unsubstituted aralkyl group;

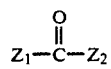      Formula (D-3)

-continued

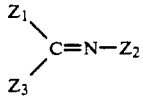      Formula (D-4)

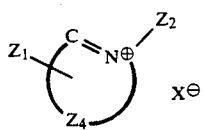      Formula (D-5)

wherein $Z_1$ and $Z_2$ are each a bond to AF or a hydrogen atom, an alkylamino group, an alkyl group having 1 to 20 carbon atoms, an aryl group having 6 to 20 carbon atoms, an acylamino group, or a 4- or 7-membered substituted or unsubstituted heterocyclic group containing, as the hetero atom, a nitrogen atom, a sulfur atom, or an oxygen atom; $Z_3$ is a hydrogen atom, a halogen atom, an alkyl group having 1 to 20 carbon atoms, an aryl group having 6 to 20 carbon atoms, a heterocyclic group, an alkoxy group an acyl group, a carbamoyl group, a sulfamoyl group, a sulfonyl group, an alkoxycarbonyl group, an acylamino group, a sulfonamido group, an alkylthio group, or a ureido group; or $Z_1$ and $Z_3$ are taken together to form a ring; $Z_4$ is a group of atoms selected from the group consisting of a carbon atom, a nitrogen atom, an oxygen atom, and a sulfur atom, which can form a 5- or 6-membered unsaturated heterocyclic ring; and $X^\ominus$ is an organic sulfonic acid anion, an organic carboxylic acid anion, a halogen ion, or an inorganic anion;

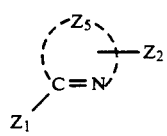      Formula (D-6)

wherein $Z_1$ and $Z_2$ are as defined above; and $Z_5$ is a group of atoms selected from the group consisting of a carbon atom, an oxygen atom, and a nitrogen atom, which, together with

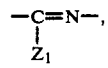

can form a 5- to 7-membered ring and which does not give aromatic group properties to

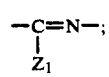

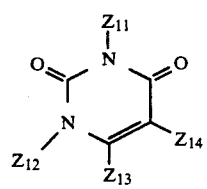      Formula (D-7)

-continued

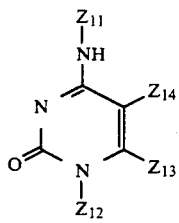
Formula (D-8)

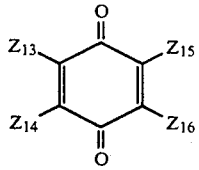
Formula (D-9)

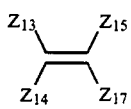
Formula (D-10)

wherein at least one of $Z_{11}$ to $Z_{17}$ is one of those groups defined for AF or a group containing an AF group; $Z_{11}$ and $Z_{12}$ are each a hydrogen atom, an alkyl group having 1 to 20 carbon atoms, a aryl group having 6 to 20 carbon atoms, or an AF group; $Z_{13}$, $Z_{14}$, $Z_{15}$, and $Z_{16}$ are each a hydrogen atom, an alkyl group having 1 to 12 carbon atoms, an aryl group having 6 to 20 carbon atoms, a halogen atom, an aryloxy group, an arylthio group, an alkylthio group, an alkoxycarbonyl group, an aryloxycarbonyl group, an alkanesulfonyl group, a sulfamoyl group, a carbamoyl group, a ureido group, an acyl group, an acylamino group, an arylsulfonyl group, a heterocyclic group, an acyloxy group, a nitro group, a cyano group, a carboxyl group, a thiocarbamoyl group, a sulfamoylamino group, a diacylamino group, or an AF group; $Z_{17}$ is a halogen atom, an alkoxycarbonyl group, an aryloxycarbonyl group, an alkanesulfonyl group, a sulfamoyl group a carbamoyl group, an acyl group, a diacylamino group, an arylsulfonyl group, a heterocyclic group, a nitro group, a cyano group, a carboxyl group, or a sulfonamido group, provided that AF can be bonded through one of the foregoing groups which can form a divalent group; in formula (D-9), $Z_{15}$ and $Z_{16}$ can each form a divalent group and, when taken together, can form a ring; and in formula (D-10), $Z_{15}$ and $Z_{17}$ can each form a divalent group and, when taken together, can form a ring;

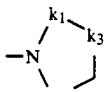
Formula (D-11)

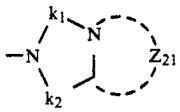
Formula (D-12)

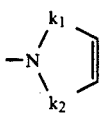
Formula (D-13)

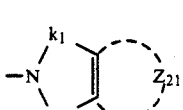
Formula (D-14)

wherein $Z_{21}$ is a saturated or unsaturated 6-membered ring; $k_1$ and $k_2$ are each an electron attractive group; $k_3$ is —N—R wherein R is an alkyl group having not more than 6 carbon atoms;

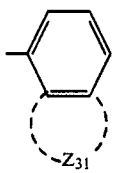
Formula (D-15)

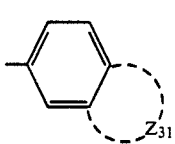
Formula (D-16)

wherein $Z_{31}$ is a group which can form a 5- or 6-membered lactone ring or a 5-membered cyclic imide.

10. A silver halide photographic material as claimed in claim 9, wherein said CCD is represented by formula (D-1).

* * * * *